(12) United States Patent
Ilan et al.

(10) Patent No.: US 10,618,950 B2
(45) Date of Patent: Apr. 14, 2020

(54) METHOD AND DEVICE FOR FAST DISSOLUTION OF SOLID PROTEIN COMPOSITION

(71) Applicants:Omrix Biopharmaceuticals Ltd., Rehovot (IL); Ethicon, Inc., Somerville, NJ (US)

(72) Inventors: Erez Ilan, Kibbutz Netzer Sereni (IL); Kfir Regev, Tel-Aviv (IL); Dana Leitman, Tel-Aviv (IL); Israel Nur, Moshav Timmorim (IL); Moti Meron, Herzliah (IL); John Goodman, Ann Arbor, MI (US)

(73) Assignees: Omrix Biopharmaceuticals Ltd., Rehovot (IL); Ethicon, Inc., Somerville, NJ (US)

( * ) Notice: Subject to any disclaimer, the term of this patent is extended or adjusted under 35 U.S.C. 154(b) by 624 days.

(21) Appl. No.: 13/722,348

(22) Filed: Dec. 20, 2012

(65) Prior Publication Data

US 2013/0312868 A1     Nov. 28, 2013

Related U.S. Application Data

(60) Provisional application No. 61/582,524, filed on Jan. 3, 2012, provisional application No. 61/677,048, filed on Jul. 30, 2012.

(30) Foreign Application Priority Data

Dec. 29, 2011   (IL) .......................................... 217273
Jul. 30, 2012   (IL) .......................................... 221180

(51) Int. Cl.
*C07K 14/75*       (2006.01)
*B01F 15/02*       (2006.01)
(Continued)

(52) U.S. Cl.
CPC .............. *C07K 14/75* (2013.01); *A61M 5/284* (2013.01); *B01F 3/12* (2013.01); *B01F 5/0685* (2013.01);
(Continued)

(58) Field of Classification Search
CPC ............ B01F 13/0023; B01F 2003/125; B01F 2003/1257; B01F 15/0258; B01F 15/0291; A61M 5/284; A61M 5/19; C07K 14/75
See application file for complete search history.

(56) References Cited

U.S. PATENT DOCUMENTS 3,052,240 A    9/1962   Silver et al.
3,405,712 A   10/1968   Pierick
(Continued)

FOREIGN PATENT DOCUMENTS

CA     1182444      2/1985
CN     1042165      5/1990
(Continued)

OTHER PUBLICATIONS

English Machine Translation of Arnitz (DE 102005017985), published Oct. 26 2006.*
(Continued)

*Primary Examiner* — Andrew D StClair
(74) *Attorney, Agent, or Firm* — David R. Crichton

(57) ABSTRACT

Provided are methods and devices for dissolving solid protein compositions, such as solid compositions comprising fibrinogen, in an aqueous solvent. The methods comprise use of a closed container containing a volume of solid fibrinogen composition and a head space wherein the pressure within the headspace is sub-atmospheric. Aqueous solvent is introduced into the container while maintain the sub-atmospheric pressure, and subsequent to addition of the
(Continued)

solvent, the size of the headspace is decreased to bring the pressure to atmospheric pressure. The devices are suitable for use in the disclosed method.

11 Claims, 8 Drawing Sheets

(51) Int. Cl.
  *B01F 3/12* (2006.01)
  *B01F 5/06* (2006.01)
  *B01F 13/00* (2006.01)
  *A61M 5/28* (2006.01)
  *A61M 5/19* (2006.01)

(52) U.S. Cl.
  CPC ...... *B01F 13/0023* (2013.01); *B01F 13/0052* (2013.01); *B01F 15/0225* (2013.01); *B01F 15/0258* (2013.01); *A61M 5/19* (2013.01)

(56) References Cited

U.S. PATENT DOCUMENTS

| | | | |
|---|---|---|---|
| 4,650,678 A | | 3/1987 | Fuhge et al. |
| 4,742,128 A | * | 5/1988 | Frisch .................. C08G 18/10 264/240 |
| 4,909,251 A | | 3/1990 | Seelich |
| 4,978,336 A | * | 12/1990 | Capozzi et al. ................ 604/82 |
| 5,122,117 A | * | 6/1992 | Haber et al. .................... 604/90 |
| 5,599,790 A | * | 2/1997 | Altieri et al. ................ 514/13.6 |
| 5,792,835 A | * | 8/1998 | Tse et al. ....................... 530/382 |
| 5,962,405 A | | 10/1999 | Seelich |
| 6,349,850 B1 | | 2/2002 | Cheikh |
| 6,965,014 B1 | * | 11/2005 | Delmotte et al. ............. 530/382 |
| 7,125,569 B2 | | 10/2006 | Nur et al. |
| 7,387,623 B2 | * | 6/2008 | MacLeod ..................... 604/416 |
| 8,211,086 B2 | | 7/2012 | Matusch |
| 2002/0094514 A1 | | 7/2002 | Bowlin et al. ..................... 435/2 |
| 2004/0005310 A1 | | 1/2004 | Rapp et al. |
| 2004/0039366 A1 | | 2/2004 | MacLeod ..................... 604/416 |
| 2008/0027097 A1 | * | 1/2008 | Kong et al. .................... 514/311 |
| 2009/0246261 A1 | * | 10/2009 | Delmotte ..................... 424/445 |
| 2010/0068196 A1 | * | 3/2010 | Nur et al. .................. 424/94.64 |
| 2010/0274279 A1 | * | 10/2010 | Delmotte ..................... 606/213 |
| 2011/0060361 A1 | * | 3/2011 | Schweiss et al. ............. 606/213 |
| 2011/0196342 A1 | | 8/2011 | Matusch |

FOREIGN PATENT DOCUMENTS

| | | |
|---|---|---|
| CN | 101394824 | 3/2009 |
| DE | 20216631 | 3/2004 |
| DE | 102005017985 | 10/2006 |
| EP | 0534178 | 4/2001 |
| EP | 1390485 | 10/2006 |
| EP | 2130549 | 12/2009 |
| JP | 3063935 | 12/1999 |
| JP | 2010-023021 | 2/2010 |
| JP | 2011-019618 | 2/2011 |
| JP | 2011-508639 | 3/2011 |
| RU | 2429056 | 9/2011 |
| SU | 1697836 | 12/1991 |
| WO | WO 1997/033633 | 9/1997 |
| WO | WO 08/053475 | 5/2008 |
| WO | WO 2009/083089 | 7/2009 |
| WO | WO 2013/098805 | 7/2013 |

OTHER PUBLICATIONS

Paradossi et al, Ultrasound Contrast Agents, ISBN-13 978-8847014930 (Dec. 3, 2009).*
Myers, The Basics of Chemistry, ISBN-13 978-0313361340 (Jun. 30, 2003).*
Gerard Marx et al., "Heat Denaturation of Fibrinogen to Develop a Biomedical Matrix", published Apr. 30, 2007.*
John Kieffer, "60th Conference on Glass Problems", Chapter 4. Foaming of Glass Melts, published Mar. 26, 2008.*
International Search Report re: PCT/IL2012/000393 dated Apr. 5, 2013.
Clauss. Gerinnungsphysiologische Schnellmethode zur Bestimmung des Fibrinogens. Acta Haematologica 1957 vol. 17 pp. 237-246.
Mosesson et al 'The Preparation and Properties of Human Fibrinogen of Relatively High Solubility' Biochemistry, 1966, vol. 5, No. 9 pp. 2829-2835.
Parker et al 'Determination of the Influence of Primary Drying Rates on the Microscale Structural Attributes and Physicochemical Properties of Protein Containing Lyophilized Products' Journal of Pharmaceutical Sciences. 2010 vol. 99, No. 11 pp. 4616-4629.
Fibrin sealant kit' *European Pharmacopaiea* Third Edition 1997; 0903 pp. 858, Council of Europe in Strasbourg.
International Preliminary Report on Patentability re: PCT/IL2012/000393 dated Jul. 1, 2014.
Stigler, J. et al 'Protein Interactions with Microballoons: Consequences for Biocompatibility and Application as Contrast Agents' (2010) Chapter: 5 pp. 53-66.

* cited by examiner

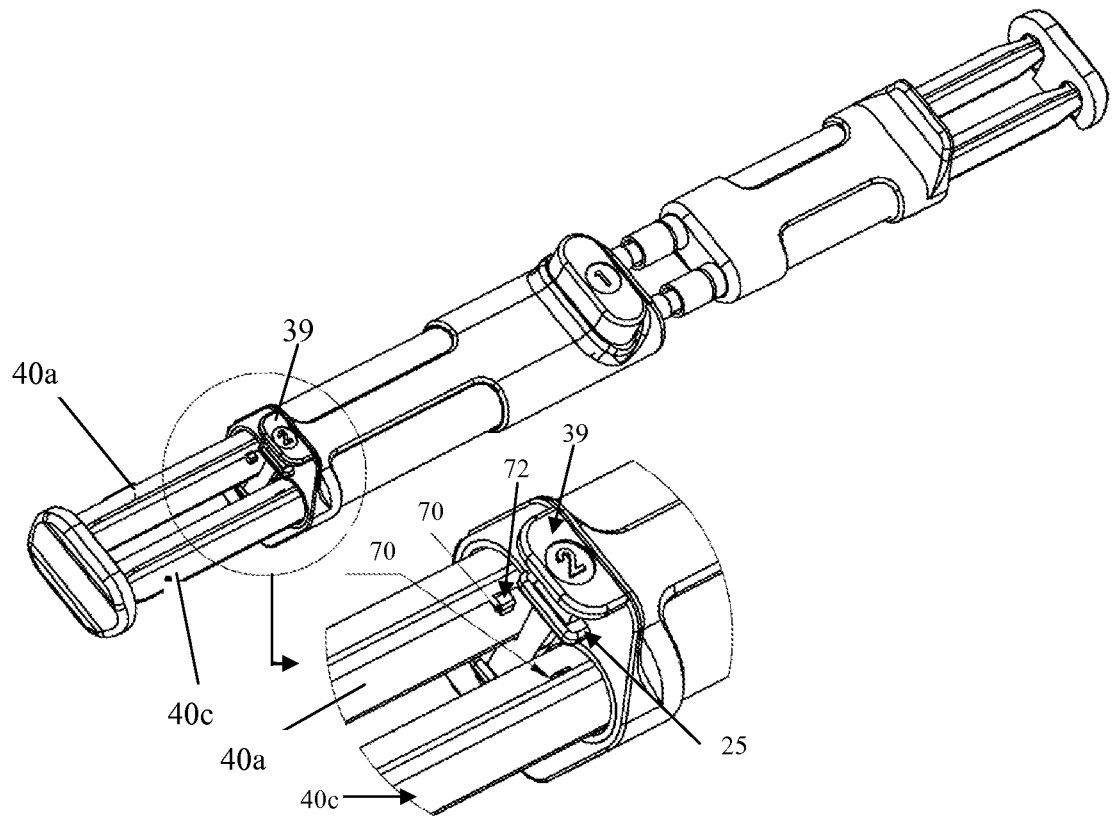
Fig. 9A
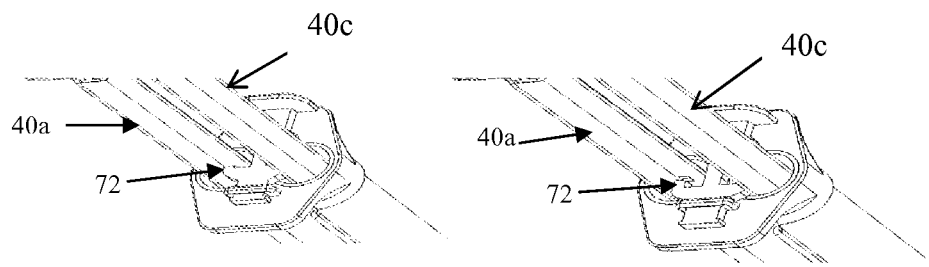
Fig. 9B                    Fig. 9C

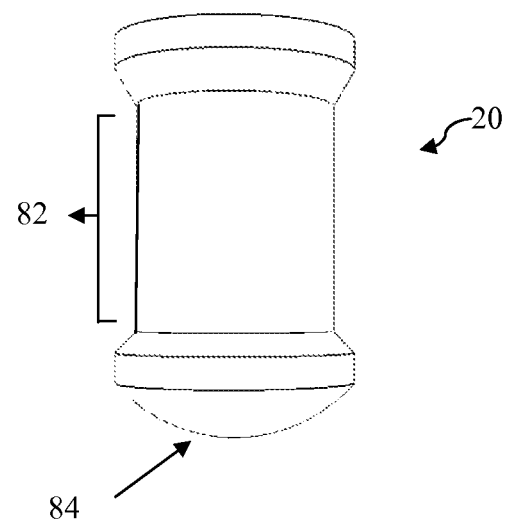
Fig. 10
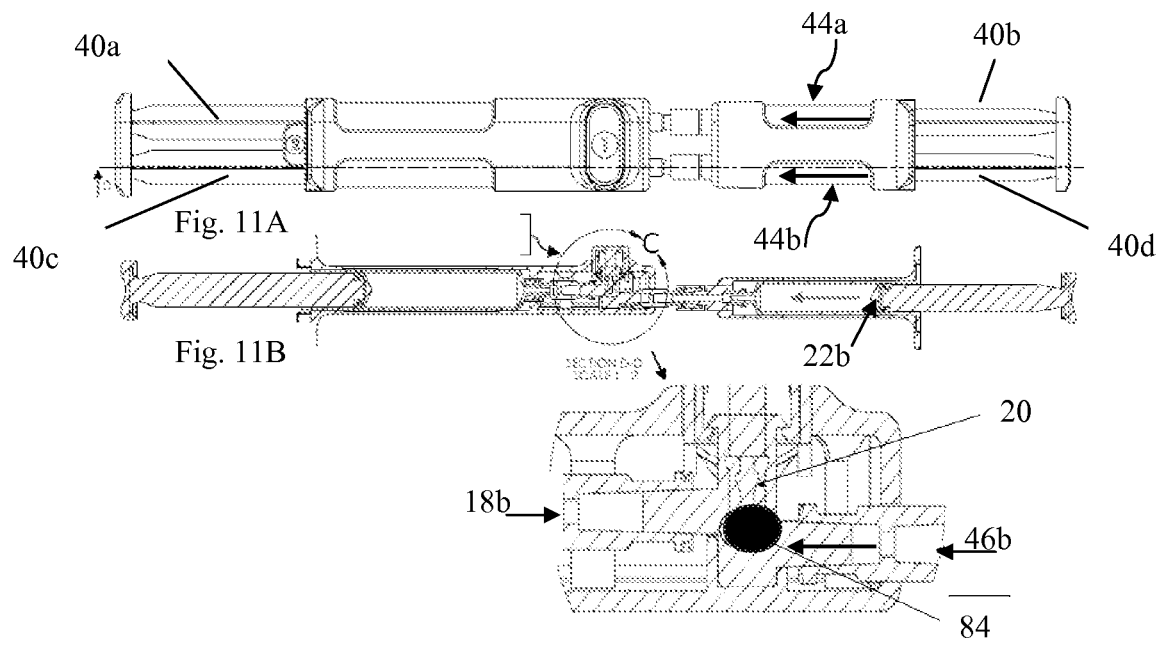
Fig. 11A
Fig. 11B
Fig. 11C

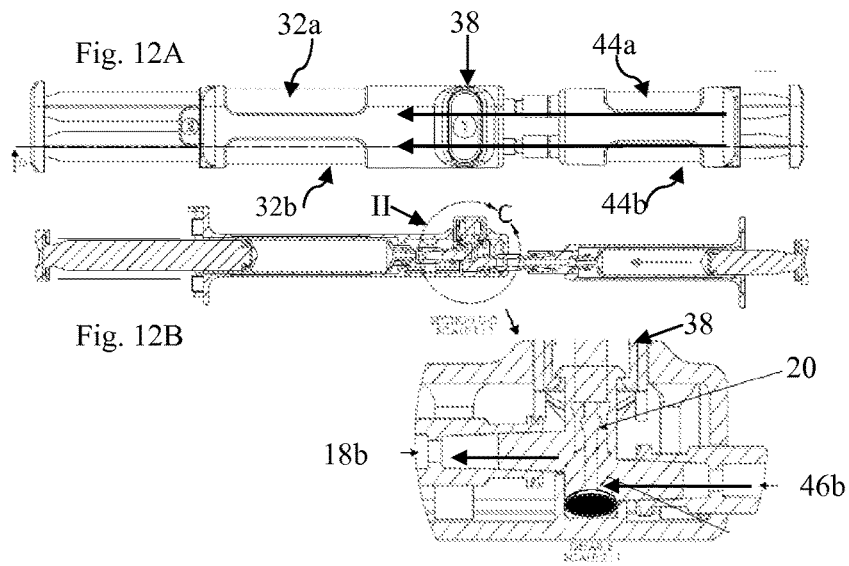
Fig. 12A
Fig. 12B
Fig. 12C
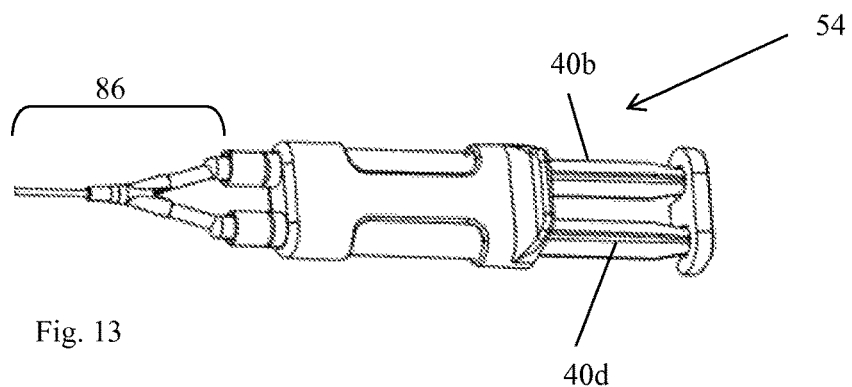
Fig. 13
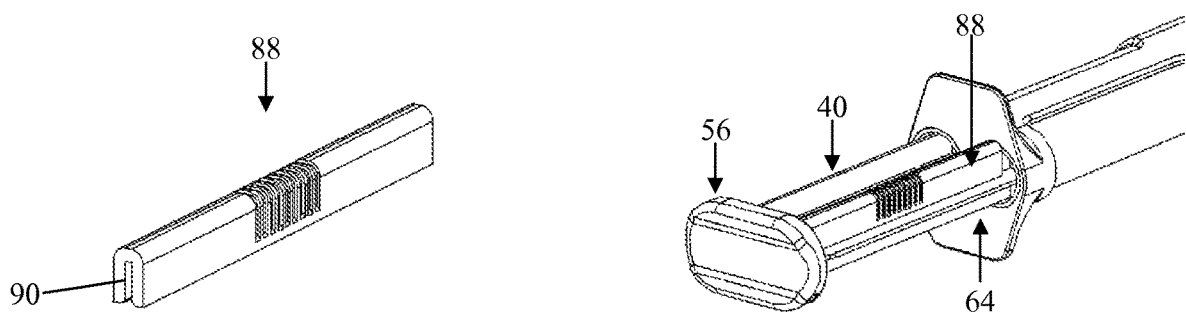
Fig. 14A
Fig. 14B

METHOD AND DEVICE FOR FAST DISSOLUTION OF SOLID PROTEIN COMPOSITION

This application is a Non-Provisional that claims the benefit of U.S. Provisional Application Ser. No. 61/582,524, filed Jan. 3, 2012 and U.S. Provisional Application Ser. No. 61/677,048, filed Jul. 30, 2012, the disclosure of which is hereby incorporated by reference herein. The present application also claims benefit of Israeli Patent Application Number IL 217273, filed Dec. 29, 2011 and Israeli Patent Application Number IL 221180, filed Jul. 30, 2012.

FIELD OF THE INVENTION

The invention relates to the field of preparation of pharmaceutical compositions, and more particularly, to methods and devices for dissolving solid protein compositions, such as solid compositions comprising fibrinogen, in an aqueous solvent.

BACKGROUND OF THE INVENTION

Fibrinogen is an important component in the preparation of fibrin sealant, which is used for preventing leakage of fluids, such as air and/or liquid e.g. blood from tissues. Fibrinogen is converted to fibrin by an enzymatic reaction involving thrombin and factor XIII.

Fibrinogen may be converted to a solid form, for example by lyophilization, prior to storage, in order to reduce protein degradation. A solid fibrinogen preparation has the advantage that it can be stored over a relatively long period of time at a temperature of at least 4° C., such as at room temperature, while retaining its biological activity. For therapeutic use, the solid fibrinogen is typically dissolved in an aqueous solvent prior to use. Solutions with high fibrinogen concentration are often required, e.g. when using the fibrinogen as a component of fibrin sealants together with a thrombin component, since typically adhesive strength is proportional to the fibrinogen concentration.

Fibrinogen is among the least soluble of the plasma proteins (The Preparation and Properties of Human Fibrinogen of Relatively High Solubility*M. W. Mosesson, Sol Sherry Biochemistry, 1966, 5 (9), pp 2829-2835). Thus, it is difficult and time consuming to dissolve a solid fibrinogen preparation to obtain a solution with high fibrinogen concentration e.g. at least 40 mg fibrinogen/ml. The problem is further complicated when foam forms and disappears slowly during dissolution of the solid fibrinogen composition. The presence of foam can further prolong the dissolution time and/or negatively affect the fibrinogen functionality, and the mechanical properties of the fibrin sealant prepared with the fibrinogen solution.

Background art includes U.S. Pat. Nos. 6,349,850; 4,650,678; 4,909,251; and 5,962,405; U.S. Patent Publication No. 2004/0005310; and European Patent Publication No. EP 2130549A1.

There is an unmet need for a method and a device enabling fast dissolution of solid fibrinogen to form a high concentrated fibrinogen solution without the addition of excipients to increase the solubility of fibrinogen.

SUMMARY OF THE INVENTION

Provided herein are methods and devices for dissolving solid protein compositions, such as solid fibrinogen compositions, in an aqueous solvent.

The present inventors have found that dissolving a solid fibrinogen composition, such as a lyophilized "cake" having low protein density, in an aqueous solvent, resulted in higher dissolution level and faster dissolution, as compared to use of a higher protein density "cake". It was further found that adding the aqueous solvent to the solid composition at sub-atmospheric pressure, followed by equilibration to atmospheric pressure without allowing entry of air to the container in which solubilization was carried out during the solubilization process, minimized or avoided the presence of the foam.

As used herein, the term "solid composition" refers to a composition having a water content of equal to or less than about 5% (w/w) water such as equal to or less than 3%, based on the total weight of the solid composition.

Aspects and embodiments of the invention are described in the specification hereinbelow and in the appended claims.

According to an aspect of some embodiments of the invention, there is provided a method for dissolving a solid fibrinogen composition in an aqueous solvent, comprising the steps of providing a closed container containing a volume of the solid fibrinogen composition and a headspace, wherein the pressure within the headspace is a sub-atmospheric pressure; while maintaining the internal pressure in the headspace at sub-atmosphere pressure, introducing into the container a volume of an aqueous solvent which is less than the volume of the solid fibrinogen composition, to form a solution comprising at least 40 mg fibrinogen/ml; and subsequently decreasing the size of the headspace in the container until the pressure in the headspace equals atmospheric pressure.

In some embodiments, the method further comprises agitating the container.

The method disclosed herein provides a solution comprising a high fibrinogen concentration of at least 40 mg fibrinogen/ml within equal to or less than 90 seconds. In some embodiments, the solution is obtained within about 90, 85, 80, 75, 70, 75, 70, 65, 60, 55, 50, 45, 40, or 30 seconds. In one embodiment, a concentrated fibrinogen solution is obtained within a time range of from about 45 to about 90 seconds.

The solid compositions disclosed herein comprise a protein, such as fibrinogen, in a solid state. In some embodiments, the solid fibrinogen compositions described herein comprise fibrinogen as the main ingredient, but may further include other ingredients e.g. other proteins. The fibrinogen in the composition can be blood-derived or recombinant. Examples of proteins other than fibrinogen present in the composition include, but are not limited to, fibronectin, factor VIII, von Willebrand factor, and factor XIII. In one embodiment of the invention, the composition is derived from a cryoprecipitate. In one embodiment of the invention, plasminogen is specifically removed from the cryoprecipitate in order to delay or stop the fibrinolysis (as described in U.S. Pat. Nos. 5,792,835 and 7,125,569).

In some embodiments, the fibrinogen composition comprises human fibrinogen (also referred to herein as BAC, Biological Active Component). BAC can be a concentrated viral-inactivated cryoprecipitate of human plasma prepared as described in European Patent No. 534,178), incorporated by reference as if fully set forth herein, which consists mainly of fibrinogen (approx. 85%). The composition can be plasminogen-depleted, as in EP patent 1,390,485, incorporated by reference as if fully set forth herein, in which case anti-fibrinolytic agents may not be included. In one embodiment of the invention, BAC is provided as a solid lyophilized "cake"

The term "cryoprecipitate" refers to a blood derived component which is obtained from frozen plasma prepared from whole blood, recovered plasma or from source plasma which is collected by plasmapheresis. A cryoprecipitate can be obtained when frozen plasma is thawed in the cold, typically at a temperature of 0-4° C., resulting in the formation of a precipitate that contains fibrinogen and factor XIII. The precipitate can be collected, for example, by centrifugation.

Non-limiting examples of forms of solid compositions which may be dissolved using the methods and devices described herein include, but are not limited to, lyophilized "cakes", solid particles, particle dispersion, powder, and flakes. Solid compositions may be produced having different protein densities.

In some embodiments, the solid fibrinogen composition is a lyophilized cake. The fibrinogen density within the lyophilized "cake" can be decreased to about 5 mg/cc while maintaining the stability of the lyophilizate without any collapse of the "cake" (Parker et. al. "Determination of the influence of primary drying rates on the microscale structural attributes and physicochemical properties of protein containing lyophilized products". J Pharm Sci. 2010; 99:4616-4629). Typically, a solid "cake" of at least 5 mg fibrinogen/cc can substantially support its own structure without collapsing.

In some embodiments, the density of fibrinogen in the solid fibrinogen composition is in the range of from about 5 to lower than about 63 mg/cc, such as equal to or less than about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62 mg/cc. In one embodiment, the solid fibrinogen composition has a fibrinogen density of not more than about 23 mg/cc.

The solid, such as a lyophilized "cake", can be prepared from a fibrinogen-containing solution having a fibrinogen concentration in the range of about 5 to lower than about 63 mg/ml such as equal to or less than 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, and 62 mg/ml. Typically, the volume of the resulting "cake" is equal to the volume of the fibrinogen-containing solution used to prepare the "cake".

In some embodiments, the solid fibrinogen composition is obtained from a BAC stock solution, such as a BAC stock solution (for example the fibrinogen component in EVI-CEL™) having a fibrinogen concentration of about 63 mg/ml. In some embodiments, the solid fibrinogen is obtained by lyophilization of the BAC stock solution.

In some embodiments, the high fibrinogen concentration in the solution obtained by dissolving the solid fibrinogen composition in the aqueous solvent is in the range of from about 40 to about 120 mg fibrinogen/ml, such as, for example, about 40, 41, 45, 50, 55, 60, 65, 70, 75, 80, 85, 90, 95, 100, 105, 110, 115, or 120 mg fibrinogen/ml. In one embodiment, a concentrated fibrinogen solution comprising fibrinogen at a concentration in the range of from about 63 to about 70 mg/ml is obtained. The fibrinogen is substantially completely dissolved.

In some embodiments, the aqueous solvent is Water for Injection, substantially devoid of excipients. In some embodiments, the aqueous solvent is degassed prior to introduction into the container comprising the solid composition.

In order to dissolve the "cake" in the aqueous solvent, a solid dispersion can optionally be prepared by mechanically crushing the "cake". The dispersion can optionally be introduced into a milling device to produce fine powder as described in WO08/053,475, the content of which is incorporated by reference as if fully set forth herein.

The aqueous solvent comprises water (in some embodiments, at least 50% water by volume) and in some embodiments may optionally comprise additional ingredients such as buffering agents and/or other excipients, such as pharmaceutically acceptable excipients (including, for example, one or more selected from the group consisting of arginine hydrochloride, glycine, sodium chloride, sodium citrate, and calcium chloride). The water can be, for example, BWFI (Racteriostetic Water for Injection), SWFI (Sterile Water for Injection) and the like.

The protein dissolution level in the solution formed by dissolving the solid fibrinogen composition in aqueous solvent can be measured as described below in the Materials and Methods section under "Measurements of Protein dissolution level". The presence of foam can be visually inspected.

In some embodiments, the internal pressure in the headspace is initially lower than about 500 mBar, such as, for example, equal to or lower than about 500, 450, 400, 350, 300, 250, 200, 150, 100, 50, 25, 20, 15, 10, 5, 1, 0.5 or 0.12 mBar. In one embodiment, the internal pressure in the headspace is not more than about 0.12 mBar.

In some embodiments, the internal pressure within the closed container is brought to a desired sub-atmospheric pressure by in a programmable lyophilization device by programming the device to attain the desired internal pressure, and closing the container when the desired pressure is attained.

In some embodiments, the internal pressure within the closed container is brought to a desired sub-atmospheric pressure by withdrawing air from the closed container e.g. by using a vacuum pump. In some embodiments, in order to monitor and/or adjust the pressure within the container, an electronic vacuum gauge or electronic manometer is used.

In one embodiment, a solid fibrinogen composition having a fibrinogen density of about 21 mg/cc is dissolved in solvent, wherein the pressure in the headspace is about 0.12 mBar.

In some embodiments, the container comprises at least two distinct portions in mutual fluid communication, a first portion containing the aqueous solvent, and a second portion containing the solid fibrinogen composition, wherein the aqueous solvent is introduced from the first distinct portion to the second distinct portion of the container.

In some embodiments, the aqueous solvent is contained within a reservoir, wherein the container and the reservoir are in mutual fluid communication, and wherein agitating comprises repeatedly transferring the aqueous solvent between the container and the reservoir.

In some embodiments, agitating comprises manually shaking the container. In some such embodiment, at least one sphere of an inert solid material, having density greater than that of the solution, (such as a metal, for example stainless steel), is introduced into the container prior to manually shaking. In some embodiments, the sphere comprises a bead having diameters in the range of from about 3 to about 7 mm.

In some embodiments, a time interval of at least 5 seconds (such as, for example, at least 6, 7, 8, 9, 10, 11, 12, 13, 14, 15, 16, 17, 18, 19 or 20 seconds), is allowed to elapse between completion of introducing the solvent into the container and commencement of decreasing the volume of the headspace. In some embodiments, the time interval is at least about 20 seconds.

In some embodiments, after decreasing the volume of the headspace, the solution is incubated in the container (i.e. allowed to stand prior to use), for example for a time period of no longer than about 2 minutes.

The methods described herein may be carried out using any suitable devices or containers including, but not limited to, bottles, lyophilization vessels, barrels, jars, and syringes known in the art. In some embodiments, the methods are carried out using the devices described below.

According to an aspect of some embodiments of the invention, there is provided a device suitable for dissolving a solid composition in an aqueous solvent, the device comprising a first closed container suitable for holding a first solid composition, the first closed container including a first closed container inlet having a closed state and an open state, wherein in the closed state the first closed container inlet is sealed to the passage of fluid and in the open state the first closed container inlet provides a path for fluid communication into the first closed container. The device further comprises a first movable seal element arranged within the first closed container, for sealing the first closed container and configured to maintain sealing of the first closed container while moving therein between at least a first and a second position within the first closed container, to decrease the internal volume of the first closed container. The device further comprises a holding element configured to releasably hold the first movable seal element in a first position within the first closed container, and a first controller for controlling changing of the first closed container inlet between a closed state and an open state.

Optionally, when the first closed container inlet is in a closed state while the first movable seal element is in the second position, and subsequently the first movable seal element is moved to the first position and the first holding element holds the first movable seal element, a headspace having a sub-atmospheric pressure is formed. Alternatively, the device is provided with the closed container further containing a headspace with a sub-atmospheric pressure; a closed container inlet; and the holding element holding the first movable seal element in the first position.

In some embodiments, the device further comprises a first reservoir [42a] suitable for holding a first aqueous solvent; and a second moveable seal element arranged within the first reservoir configured to maintain sealing of the first reservoir, the first reservoir comprising a first reservoir outlet adapted to be in fluid communication (directly or indirectly) with the first closed container inlet.

In some embodiments, the first closed container is a first syringe barrel having a front end and a back end, wherein the front end comprises the first closed container inlet, and wherein the first moveable seal element comprises a first piston arranged within the first syringe barrel slidingly displaceable from the back end towards the front end of the first syringe barrel and connected to a first piston rod.

In some embodiments, the first reservoir comprises a second syringe barrel having a front end and a back end, wherein the front end comprises the first reservoir outlet, and the second moveable seal element comprises a second piston arranged within the second syringe barrel slidingly displaceable from the back end towards the front end of the second syringe barrel and connected to a second piston rod.

In some embodiments, wherein when the inlet is in an open position and wherein when the holding element releases the first movable seal, the first movable seal moves from a first to a second position within the first closed container, thereby decreasing the internal volume of the first closed container, wherein the internal pressure within the first closed container is increased.

In some embodiments, the device further comprises a second closed container suitable for holding a second solid composition, the second closed container including a second closed container inlet having a closed state and an open state, wherein in the closed state the second closed container is sealed to the passage of fluid and in the open state the second closed container inlet provides a path for fluid communication into the second closed container. In such embodiments, the device further comprises a third movable seal element arranged within the second closed container, for sealing the second closed container and configured to maintain sealing of the second closed container while moving therein between at least a first and a second position within the second closed container, to decrease the internal volume of the second closed container. In such embodiments, the device further comprises a holding element configured to releasably hold the third movable seal element in a first position within the second closed container, and a second controller for controlling changing of the second closed container inlet between a closed state and an open state. Optionally, a single holding element may releasably hold both the first and the third movable seal elements in a first position. Alternatively, the device may further comprise a second holding element for holding the third movable seal element. The device is provided with the second closed container further containing a headspace with a sub-atmospheric pressure; a closed container inlet; and the holding element holding the third movable seal element in the first position, or when the second closed container inlet is in a closed state while the third movable seal element is in the second position, and subsequently the third movable seal element is moved to the first position and the holding element holds the third movable seal element, a headspace having a sub-atmospheric pressure is formed.

In some embodiments, the device further comprises a second reservoir [42b] suitable for holding a second aqueous solvent and a fourth moveable seal element arranged within the second reservoir configured to maintain sealing of the second reservoir, the second reservoir comprising a second fluid outlet adapted to be in fluid communication with the second closed container inlet.

In some embodiments, the first closed container is a first syringe barrel having a front end and a back end, wherein the front end of the first syringe barrel comprises the first closed container inlet and wherein the first moveable seal element of the first closed container comprises a first piston arranged within the first syringe barrel slidingly displaceable from the back end towards the front end of the first syringe barrel and connected to a first piston rod. In such embodiments, the first reservoir comprises a second syringe barrel having a front end and a back end, wherein the front end of the second syringe barrel comprises the first reservoir outlet and wherein the second moveable seal element comprises a second piston arranged within the second syringe barrel slidingly displaceable from the back end towards the front end of the second syringe barrel and connected to a second piston rod. In such embodiments, the second closed container is a third syringe barrel having a front end and a back end, wherein the front end of the third syringe barrel comprises the second closed container inlet and wherein the third moveable seal element comprises a third piston arranged within the third syringe barrel slidingly displaceable from the back end towards the front end of the third syringe barrel and connected to a third piston rod. In such embodiments, the second reservoir comprises a fourth syringe barrel having a front end and a back end, wherein the front end of the fourth syringe barrel comprises the second reservoir outlet and wherein the fourth moveable seal element comprises a fourth piston arranged within the fourth syringe barrel slidingly displaceable from the back end towards the front end of the fourth syringe barrel and connected to a fourth piston rod.

In some embodiments, the device further comprises a housing for containing the first and second closed containers and/or the first and second reservoirs therein.

In some embodiments, the device further comprises a first housing for containing the first and second closed containers and/or a second housing for containing the first and second reservoirs therein.

In some embodiments, the first solid composition comprises solid fibrinogen.

In some embodiments, the second solid composition comprises solid thrombin.

In some embodiments, the first piston is attached to a piston rod comprising at least one recess, and the holding element comprises at least one protrusion/bulge configured to engage within the recess.

In some embodiments, the device further comprises a controller actuator which when actuated, causes the first controller and/or the second controller to move from the closed state to the open state.

The methods and devices disclosed herein, in at least some embodiments, enable a solid fibrinogen composition to be substantially completely dissolved within a short time (e.g. within 90 seconds or less) in an aqueous solvent, to obtain a highly concentrated fibrin solution (e.g. having a fibrin concentration of at least 40 mg/ml). In some embodiments, the method allows the fibrinogen solution to be prepared at, or close to, the time of administration to a subject e.g. within 90 seconds or less prior to administration to the subject.

In at least some embodiments, the presence of foam in the fibrinogen solution produced according to the methods and devices disclosed herein is minimal or negligible. In some embodiments, the fibrinogen solution is substantially devoid of foam.

In at least some embodiments, the method does not require the addition of excipients to increase the solubility of fibrinogen.

In at least some embodiments, the method does not include a heating step e.g. heating to above room temperature.

In at least some embodiments, no air is admitted to a container in which the solubilization is carried out.

Unless otherwise defined, all technical and scientific terms used herein have the same meaning as commonly understood by one of ordinary skill in the art to which the invention pertains. In addition, the descriptions, materials, methods, and examples are illustrative only and not intended to be limiting. Methods and materials similar or equivalent to those described herein can be used in the practices of the present invention.

As used herein, the term "solution" refers to a homogeneous mixture comprising at least one substance (solute) partially or substantially completely dissolved in a liquid solvent. By "substantially completely dissolved" is meant that the solute is at least 89% dissolved in the solvent.

As used herein, the term "dissolving" refers to incorporating a substance, such as a solid, into a liquid solvent to obtain a solution. As used herein, the terms "dissolving", "solubilizing", and "reconstituting" may be interchangeable.

As used herein, the term "atmospheric pressure" refers to the force per unit area exerted on a surface by the weight of air above that surface at a given location. Standard sea-level atmospheric pressure is 1 atmosphere, or 1000 mBar.

As used herein, the term "headspace" refers to a gaseous volume above a liquid or solid in a closed container, together with the volume of gas within the solid.

As used herein, the term "controller" refers to a component that regulates the direction and/or flow of a liquid e.g. through a passage or a pipe by providing an open inlet for flow of the liquid. The controller can be a valve, a stopcock, or the like. Alternatively, the controller may comprise a piercing element, such as a needle, for piercing a cover e.g. a rubber cap or wall of the closed container, therefore providing an open inlet.

As used herein, the term "lyophilization" refers to the process of freezing a solution and then reducing the concentration of water e.g. by sublimation to levels which do not support biological or chemical reactions. As used herein, the term "cake" or "solid cake" refers to a porous and spongy structure-like composition resulting from the lyophilization process. It is noted that a "solid cake" of at least 5 mg/cc can substantially support its own structure without collapsing. As used herein, the term "collapse" with regard to a cake refers to the point at which the cake can no longer support its own structure.

As used herein the term "excipient" refers to a substantially inert substance which is included in a pharmaceutical composition. Excipients can be added, for example, in order to ensure that the active substances of the composition retain their chemical stability and/or biological activity upon storage, to aid the manufacturing process and/or for aesthetic reasons e.g. color.

As used herein, the term "pharmaceutical composition" refers to a substance or mixture of substances for administration to a subject.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise.

In some embodiments, the methods and devices disclosed herein optionally provide at least one of the following advantages: enable a user (such as a surgeon or other medical practitioner) to rapidly dissolve solid pharmaceutical compositions, including solid compositions for the preparation of a sealant; enable formation of a solution having minimal or negligible amounts of foam; enable the use of highly porous and/or fragile lyophilized cakes as the solid composition; enable rapid formation of a highly concentrated fibrinogen solution from a solid fibrinogen composition; and enable storage, dilution and use of concentrated solid compositions. In some embodiments, the methods and devices described herein are particularly useful for storing and rapidly dissolving fibrinogen and applying the resulting solution to a patient.

BRIEF DESCRIPTION OF THE DRAWINGS

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures:

FIG. 9A illustrates an upper perspective view of the holding element of FIG. 6B, located on the housing holding the solid-containing unit, wherein the holding element is in an initial position.

FIG. 9B illustrates a bottom perspective view of the holding element of FIG. 6B, located on the housing holding the solid-containing unit, wherein the holding element is in the same initial position as in FIG. 9A.

FIG. 9C illustrates a bottom perspective view of the holding element of FIG. 6B, located on the housing holding the solid-containing unit, wherein the holding element is in a second position.

FIG. 10 illustrates a side view of an embodiment of a controller.

FIGS. 11A-C illustrate an embodiment of a device as disclosed herein in an initial position.

FIG. 11A shows an upper view; FIG. 11B shows a cross-sectional sided view; and FIG. 11C shows an enlarged view of the area comprising the controller of FIG. 11B.

FIGS. 12A-C illustrate an embodiment of the device as disclosed herein at a first step of operation according to some embodiments of the present invention. FIG. 12A shows an upper view; FIG. 12B-shows a cross-sectional sided view; and FIG. 12C shows an enlarged view of the area comprising the controller of FIG. 12B.

FIG. 13 illustrates the solvent-containing unit connected to a fluid-connector system through which dissolved compositions can be delivered.

FIG. 14A illustrates a spacer element configured to be positioned on a piston rod according to some embodiments of the present invention.

FIG. 14B illustrates the spacer shown in FIG. 14A positioned on the piston rod of the syringe of the solid-containing unit.

DESCRIPTION OF SOME EMBODIMENTS OF THE INVENTION

Figures 1A, 1B, 1C:
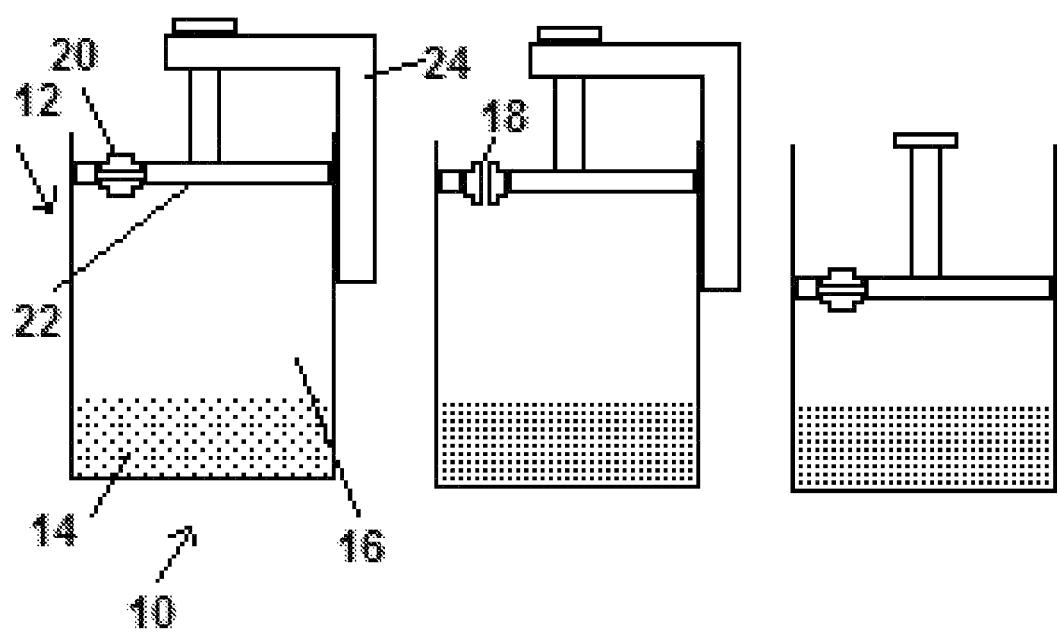
FIG. 1A is a schematic representation of a device according to the teachings disclosed herein, the device comprising a container for holding a solid composition, with an inlet, a first movable seal element arranged within the container, and a holding element which releasably holds the first movable seal element in an initial state.
FIG. 1B is a schematic representation of the device of FIG. 1A in a state wherein the inlet is changed from the initial closed state to an open state.
FIG. 1C is a schematic representation of the device of FIG. 1B, wherein the moveable seal element has moved from an initial position to a second position.

Disclosed herein are methods and devices for dissolving solid compositions comprising fibrinogen.

According to an aspect of some embodiments, there is provided a method for dissolving a solid fibrinogen composition in an aqueous solvent, comprising providing a closed container containing a volume of the solid fibrinogen composition and a headspace, wherein the pressure within the headspace is a sub-atmospheric pressure; while maintaining the internal pressure in the headspace at sub-atmosphere pressure, introducing into the container a volume of an aqueous solvent, which is less than the volume of the solid fibrinogen composition to form a solution comprising at least 40 mg fibrinogen/ml; and subsequently decreasing the size of the headspace in the container until the pressure in the headspace equals atmospheric pressure. In some embodiments, the method further comprises agitating the container. In some embodiments, the method comprises agitating the partially dissolved solution formed upon addition of the solvent to the solid composition. In some embodiments, dissolution occurs within not more than 90 seconds.

According to an aspect of some embodiments, there is provided a device suitable for dissolving a solid composition in an aqueous solvent. The device comprises a first closed container suitable for holding a first solid composition, the first closed container including a first closed container inlet having a closed state and an open state, wherein in the closed state the first closed container inlet is sealed to the passage of fluid and in the open state the first closed container inlet provides a path for fluid communication into the first closed container. The device further comprises a first movable seal element arranged within the first closed container, for sealing the first closed container and configured to maintain sealing of the first closed container while moving therein between at least a first and a second position within the first closed container, to decrease the internal volume of the first closed container. The first position is such that the headspace within the container has a sub-atmospheric pressure, and the second position is such that the headspace has a pressure equal to atmospheric pressure. The device further comprises a first holding element configured to releasably hold the first movable seal element in a first position within the first closed container. The device further comprises a first controller for controlling changing of the first closed container inlet between a closed state and an open state.

When the first closed container inlet is in a closed state and the first movable seal element is in a first position, the pressure of the first closed container is sub-atmospheric. Alternatively, when the first closed container inlet is in a closed state while the first movable seal element is in the second position, and subsequently the first movable seal element is moved to the first position and the first holding element holds the first movable seal element, a headspace having a sub-atmospheric pressure is formed.

The principles, uses and implementations of the teachings herein may be better understood with reference to the accompanying description and figures. Upon perusal of the description and figures present herein, one skilled in the art is able to implement the invention without undue effort or experimentation. In the figures, like reference numerals refer to like parts throughout.

Before explaining at least one embodiment in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways. The phraseology and terminology employed herein are for descriptive purpose and should not be regarded as limiting.

Referring now to FIGS. 1A-1C, there is shown a schematic representation of a device 10 according to the teachings disclosed herein. Device 10 comprises a closed container 12 holding a volume 14 of a solid composition, and a headspace 16. The container can be any receptacle suitable for holding the solid composition. Examples of containers include, but are not limited to, bottles, lyophilization vessels, barrels, jars, and syringes. The container is closed by a first movable seal element e.g. a rubber cap. The container can be made of any suitable material such as glass, plastic, metal and the like.

Closed container 12 comprises an inlet 18 for controlling passage of an aqueous solvent into the interior volume of closed container 12. Inlet 18 has a closed state, wherein flow of aqueous solvent into the interior volume of container 12 is blocked, and an open state wherein inlet 18 provides a path for flow of aqueous solvent into the interior volume of container 12. A controller 20 controls change of inlet 18 from the open state to the closed state. Alternatively, in some embodiments, controller 20 comprises a piercing element, such as a needle attached to a syringe comprising an aqueous solvent (not shown), and an open state of inlet 18 is provided in a cap of closed container 12 by piercing the cap with the piercing element.

Arranged within container 12 is a moveable seal element 22, for sealing container 12. Moveable seal element 22 can be moved within container 12 to change the volume of the headspace 16 within container 12, wherein moving seal element 22 in a direction which decreases the volume of headspace 16 increases the pressure within headspace 16. Moveable seal element 22 is releasably held in a first position within container 12 (directly or indirectly) by a holding element 24, such that when moveable seal element 22 is in the first position, the volume of headspace 16 is such that pressure within headspace 16 is sub-atmospheric. Holding element 24 is optionally connected to a holding element actuator 39 (shown in FIG. 6B), which actuates release of moveable seal element 22 from holding element 24.

Upon release, moveable seal element 22 moves to a second position, such that the volume of headspace 16 decreases, and pressure of headspace 16 increases to equal atmospheric pressure.

Figure 3:
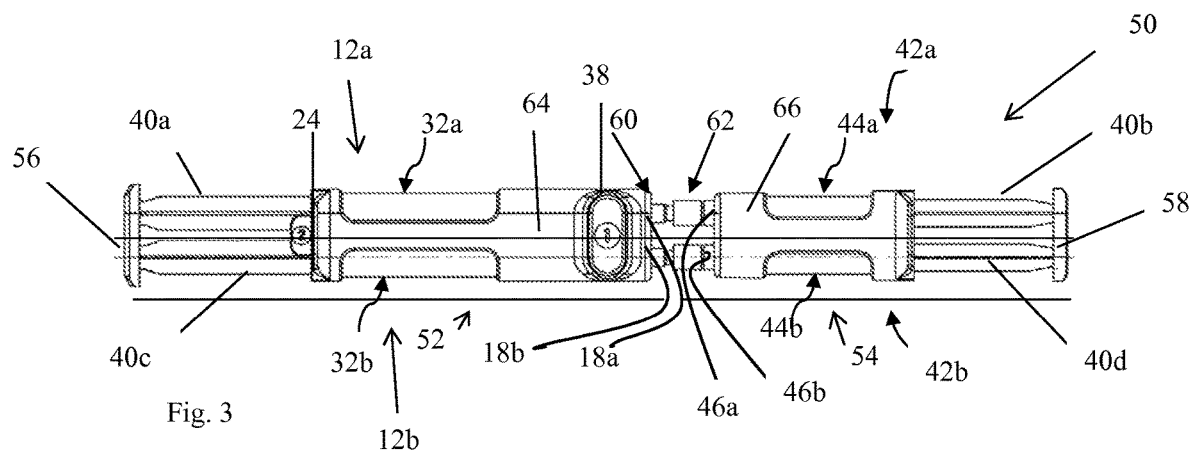
FIG. 3 illustrates an upper view of a device according to some embodiments of the present invention. The device comprises a solid-containing unit and a solvent-containing unit.

Container 12 may optionally be held within a housing 64 (shown, for example, in FIG. 3).

Device 10 may further comprise a reservoir 42 (shown, for example, in FIG. 2) for containing the aqueous solvent.

In an initial state, as shown in FIG. 1A, inlet 18 is in the closed state, holding element 24 holds moveable seal element 22 in a first position, and the pressure in the headspace 16 is sub-atmospheric.

FIG. 1B shows use of device 10, when inlet 18 is changed from the initial closed state to the open state, such that aqueous solvent is allowed to flow into the interior volume of container 12, while moveable seal element 22 is held in a first position within container 12 by holding element 24, such that pressure in headspace 16 is maintained at a sub-atmospheric level. The volume occupied by the aqueous solvent is less than the volume occupied by the solid composition As shown in FIG. 1C, after aqueous solvent has been allowed to flow into the interior volume of container 12, moveable seal element 22 is released from holding element 24, and moves within container 12 to a second position such that the volume of headspace 16 is decreased and pressure within headspace 16 increases proportionately, until atmospheric pressure is reached.

According to some embodiments, closed container 12 comprises a syringe barrel, and moveable seal element 22 comprises a plunger at least partially enclosed within the barrel. In some such embodiments, a holding element 24 releasably holds the plunger in a first position prior to use.

Figure 2:
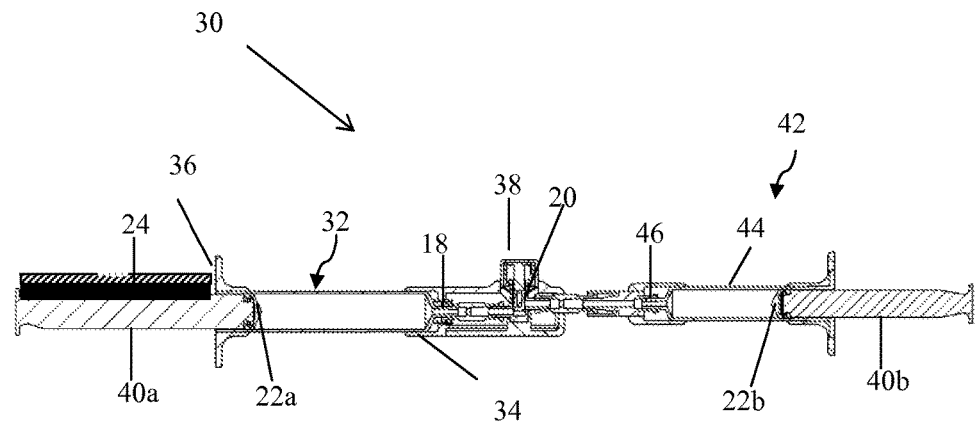
FIG. 2 illustrates a cross-sectional side view of a device according to some embodiments of the present invention, the device comprising a container for holding a solid composition, with an inlet, a first movable seal element arranged within the container, a holding element which releasably holds the first movable seal element, a first controller, a reservoir for holding a solvent, with an outlet opening and a second movable seal element arranged within the reservoir.

Referring now to FIG. 2, there is shown a cross-sectional side view of an exemplary device 30, a first syringe barrel 32 having a front end 34 having an inlet 18 and a back end 36, a first moveable seal element 22a arranged within first syringe barrel 32, a holding element 24 for releasably holding first moveable seal element 22a, and a controller 20 for changing inlet 18 from a closed state to an open state. Controller 20 is indirectly or directly connected to a controller actuator 38, which when actuated causes controller 20 to change inlet 18 from a closed state to an open state.

First moveable seal element (FIG. 2) 22a comprises a first slideably displaceable piston having a first piston rod 40a extending out of the back end of syringe barrel 32 for operating the first piston.

In some embodiments, holding element 24 comprises a spacer placed between a back end of piston rod 40a and the back end 36 of first syringe barrel 32, preventing piston rod 40a from moving forward into first syringe barrel 32. Holding element 24 is optionally connected to an actuator (not shown), which, when actuated, causes holding element 24 to release first moveable seal element 22a.

Figure 6A:
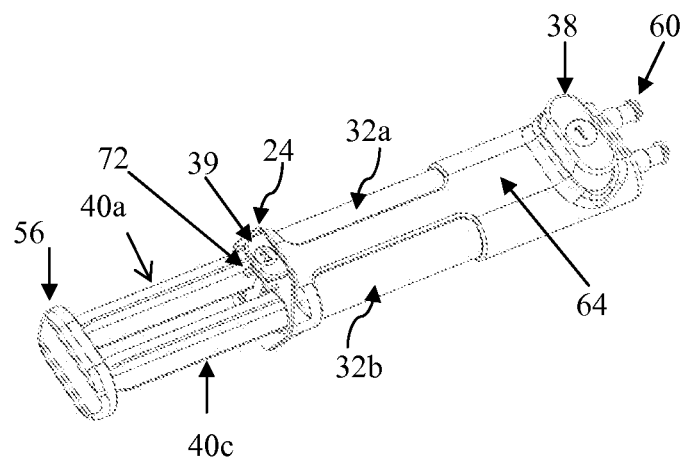
FIG. 6A illustrates a perspective view of the solid-containing unit of FIG. 3.
Figure 6B:
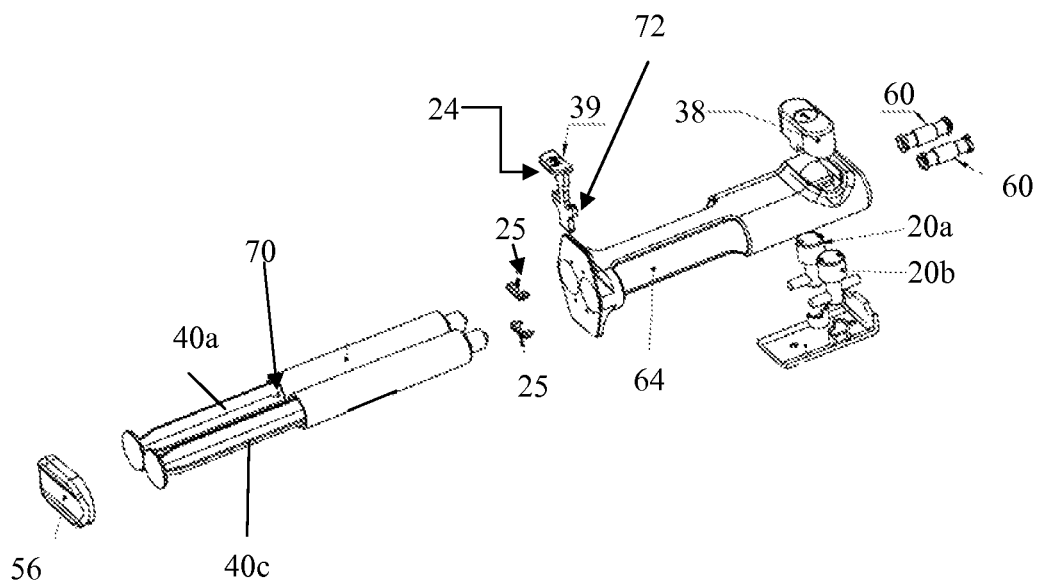
FIG. 6B illustrates an exploded view of the solid-containing unit of FIG. 3, including an embodiment of a holding element.
Figure 7A:
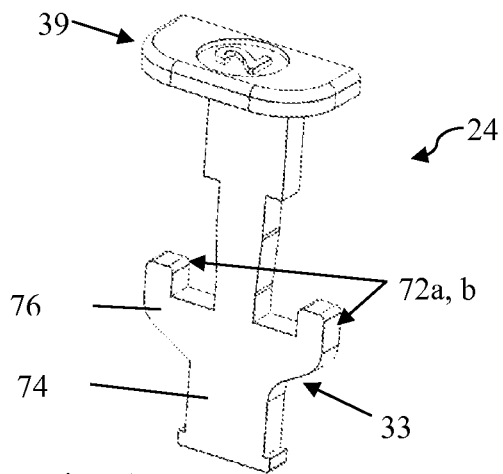
FIG. 7A illustrates a perspective and enlarged view of the holding element of FIG. 6B.
Figure 7B:
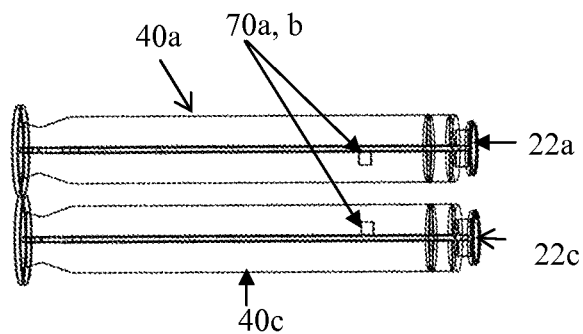
FIG. 7B illustrates a perspective view of the piston rods of the syringes of the solid-containing unit of FIG. 3.

In some embodiments, a recess is provided in piston rod 40a, and holding element 24 comprises at least one protrusion 72 (as shown in FIGS. 6B and 7A) configured to be reversibly engaged within the recess 70 (as shown in FIG. 7B).

In some embodiments, device 30 (e.g. FIG. 2) further comprises a reservoir 42 comprising a second syringe barrel 44, for containing an aqueous solvent prior to use, and a second moveable seal element 22b arranged within barrel 44 for sealing reservoir 42. Arranged within barrel 44 is a second movable seal element 22b, comprising a second slidably displacable piston having a second piston rod 40b extending out of the back end of syringe barrel 44 for operating the second piston.

Reservoir 42 comprises an outlet 46 directly or indirectly connected to inlet 18. In some embodiments, closed container 12 and reservoir 42 are configured to allow agitation of the aqueous solvent following addition to the solid composition, to facilitate dissolving of the solid composition in the solvent. In some embodiments, closed container 12 and reservoir 42 are configured to allow agitation by repeated transfer of the aqueous solvent (and of a suspension comprising partially-dissolved solution formed after addition of the aqueous solvent to the solid composition) between reservoir 42 and container 12.

Controller 20 is optionally located between inlet 18 and outlet 46.

FIG. 3 illustrates an upper view of a device 50 according to some embodiments of the present invention, wherein device 50 comprises a solid-containing unit 52 for containing solid compositions and a solvent-containing unit 54 for containing solvents.

Solid-containing unit 52 comprises two closed containers 12a, 12b, each comprising a syringe barrel 32a, 32b, having an inlet 18a, 18b, each syringe barrel 32a, 32b configured for containing a different solid composition (for example, thrombin and fibrinogen, respectively). Solvent-containing unit 54 comprises two reservoirs, each containing a syringe barrel 44a, 44b, having an outlet 46a, 46b, each syringe barrel 44a, 44b configured for containing a solvent for dissolving the solid compositions contained in syringe barrels 32a, 32b, respectively. Syringe barrels 44a, 44b can contain the same or different aqueous solvents.

Syringe barrels 32a, 32b, 44a, 44b each have a moveable seal element 22a, 22c, 22b, 22d (not shown), respectively, arranged therein, and a holding element 24, for releasably holding at least one of moveable seal elements 22a, 22c, and at least one controller 20 for changing at least a first of inlets 18a, 18b from a closed state to an open state. In some embodiments, controller 20 changes both inlets 18a, 18b from a closed state to an open state. Device 50 may optionally comprise a second controller 20b for changing a second of inlets 18a, 18b from a closed state to an open state. Controllers 20a, 20b (shown in FIG. 6B) are optionally situated between inlet 18a and outlet 46a, and between inlet 18b and outlet 46b, respectively.

Device 50 comprises a housing 64 for holding solid-containing unit 52, and a housing 66 for holding solvent-containing unit 54. Alternatively, solid-containing unit 52 and solvent-containing unit 54 may both be held within a single housing (not shown). Further alternatively, at least one of solid-containing unit 52 and solvent-containing unit 54 may be provided without a housing. Holding element 24 is optionally located within/on housing 64. Controllers 20a and/or 20b are optionally located within housing 64.

In some embodiments, controller 20 is connected to a controller actuator 38, which when actuated causes controller 20 to change at least a first of inlets 18a, 18b from a closed state to an open state. Alternatively, in some embodiments, comprising a first controller 20a and a second controller 20b, each controller 20a, 20b comprises or is connected to a controller actuator 38a, 38b, respectively, and controllers 20a, 20b are optionally positioned beneath controller actuators 38a, 38b. Alternatively, in some embodiments, a single controller actuator 38 is connected to and controls both first controller 20a and second controller 20b as shown in FIGS. 6A and 6B.

When device 50 is in an initial state, prior to activation of at least controller actuators 38, and actuation of controllers 20a, 20b, the inlets 18a, 18b are closed, preventing flow of aqueous solvent into syringe barrels 32a, 32b. Upon activation of controller actuator 38, at least one of controllers 20a, 20b is actuated, such that at least one of inlets 18a, 18b is changed from a closed to an open position, enabling flow of aqueous solvent into at least one of syringe barrels 32a, 32b.

Each moveable seal element 22a, 22b, 22c, 22d comprises a slideably displaceable piston having a piston rod 40a, 40b, 40c, 40d, respectively, extending out of the back end of the respective syringe barrel 32a, 44a, 32b, 44b for operating the piston.

Optionally, piston rods 40a, 40c of solid-containing unit 52 are mechanically connected via a coupling element 56, and piston rods 40b, 40d of solvent-containing unit 54 are mechanically connected via a coupling element 58, so that the pair of piston rods in each unit can move in unison.

Syringe barrels 32a, 32b of solid-containing unit 52 are reversibly connected in fluid communication with syringe barrels 44a, 44b, respectively, of solvent-containing unit 54, via fluid connectors 60, 62. The fluid connectors can be, for example, luer fittings. For example, solid-containing unit 52 may include a fluid connector 60 comprising two male luer fittings and solvent-containing unit 52 may include a fluid connector 62 comprising two female luer fittings. Syringe barrels 32a, 32b are positioned opposite syringe barrels 44a, 44b, respectively, and connected by leer fittings providing fluid communication.

When device 50 is in an initial position, the pressure in headspace 16 within each syringe barrel 32a, 32b is sub-atmospheric, inlets 18a, 18b are in a closed state, and holding element 24 holds piston rods 40a, 40c in a first position wherein the pressure in headspace 16 is maintained at a sub-atmospheric level.

In some embodiments, the steps of opening inlets 18a, 18b and thereby enabling solvent to flow into syringe barrels 32a, 32b results in an increase in pressure within headspace 16. The pressure in headspace 16 is advantageously maintained at sub-atmospheric pressure during the step of entry of solvent into syringe barrels 32a, 32b. For example, highly porous cakes with large surface area can be used for shortening the dissolution time, since collapse of such cakes by the plunger in syringe barrel 32, prior to the introduction of the solvent into syringe barrel 32, is prevented.

In some embodiments, maintaining a pressure difference between pressure in headspace 16 in syringe barrels 32a, 32b and the pressure within syringe barrels 44a, 44b while opening inlets 18a, 18b enables solvent to be spontaneously drawn into syringe barrels 32a, 32b.

According to some embodiments, when device 50 comprises two syringe barrels 32a, 32b each holding a solid composition, dissolution of the two solid compositions and an immediate and simultaneous administration of the two dissolved solid compositions (e.g. a dissolved fibrinogen comprising solution and a dissolved thrombin comprising solution) is enabled.

Figure 4:
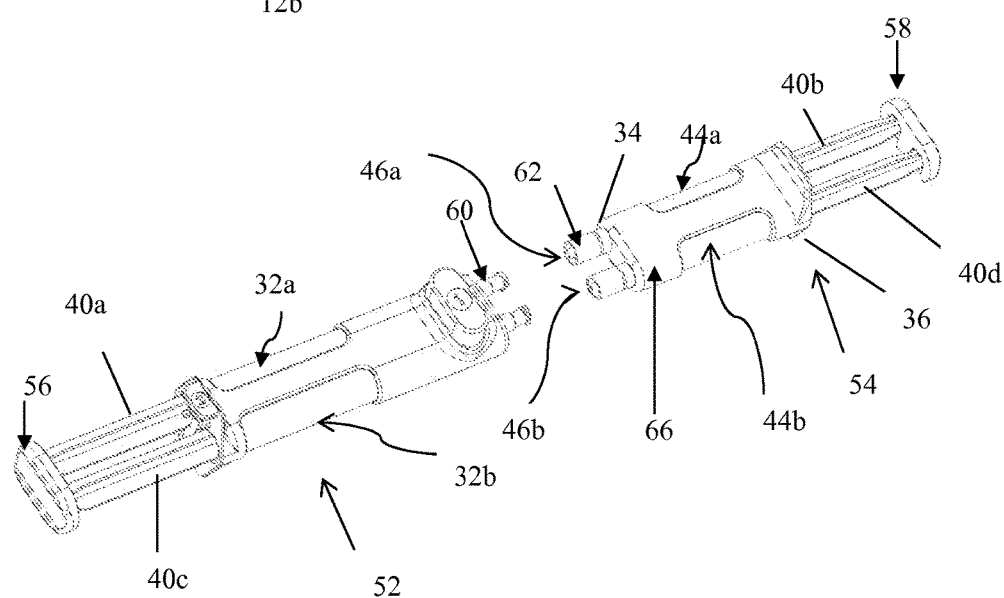
FIG. 4 illustrates a perspective view of the two units of FIG. 3 disconnected from one another.

FIG. 4 illustrates a perspective view of device 50 of FIG. 3, showing solid-containing unit 52 and solvent-containing unit 54 of FIG. 3 disconnected one from the other by detachment of fluid connector 60 comprising male leur fittings from fluid connector 62 comprising female leur fittings.

Figure 5:
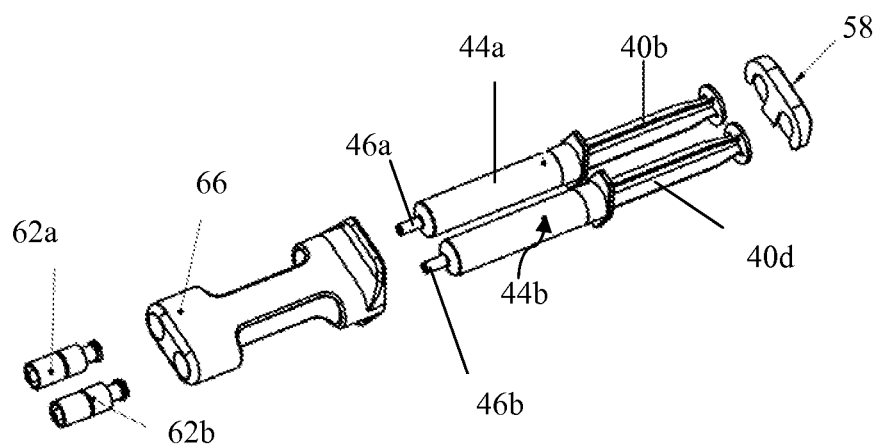
FIG. 5 illustrates an exploded view of the solvent-containing unit of the device of FIG. 3.

FIG. 5 illustrates an exploded view of an embodiment of the solvent-containing unit 54 of FIGS. 3 and 4, comprising syringe barrels 44a, 44b, a piston having a piston rod 40b, 40d, respectively, located within each syringe barrel 44a, 44b. Each syringe barrel 44a, 44b, has an outlet 46a, 46b, respectively. Syringe barrels 44a, 44b, are configured to contain a solvent. Each of syringe barrel 44a, 44b may comprise the same or different solvents.

FIG. 6A illustrates a perspective view of an embodiment of solid-containing unit 52 of FIGS. 3 and 4, contained within a housing 64 and including a holding element 24, optionally positioned on housing 64, and optionally held in place by two "U" shaped components 25 (shown in FIG. 6B), forming channel-like structures. Solid-containing unit 52 comprises two syringe barrels 32a, 32b, each configured for holding a solid composition. Each syringe barrel 32a, 32b may hold the same, or a different, solid composition. In one embodiment, syringe barrel 32a comprises a solid composition comprising fibrinogen and syringe barrel 32b comprises a solid composition comprising thrombin. Device 50 further comprises a controller actuator 38.

FIG. 6B illustrates an exploded view of the solid-containing unit 52 of FIG. 6A, wherein piston rods 40a, 40c comprise at least one recess 70 and holding element 24 (optionally positioned directly or indirectly on the back end of solid-containing unit 52 or on housing 64) comprises at least one protrusion, such as at least one bulge 72, wherein recess 70 is configured to reversibly engage bulge 72, such that when device 50 in the initial position, bulge 72 is engaged within recess 70 and holding element 24 holds at least one moveable seal element 22a, 22c in a fixed position to maintain sub-atmospheric pressure within syringe-barrel 32a, 32b of solid-containing unit 52. The location of recess 70 is determined according to the required volume of headspace 16 within barrels 32a, 32b for maintaining the desired pressure within headspace 16.

In some embodiments, each piston rod 40a, 40c comprises one recess 70a, 70b, respectively, and holding element 24 comprises two bulges 72a, 72b, each of which is configured to be engaged in one of recesses 70a and 70b, such that moveable seals 22a, 22c are retained by holding element 24, and the volume of headspace 16 in each of barrels 32a, 32b is maintained at a level providing sub-atmospheric pressure in headspace 16.

Alternatively, only a first piston rod 40a comprises a recess 70 configured to engage one bulge 72 of the holding element 24. In such embodiments, piston rod 40c is optionally connected to piston rod 40a so that both piston rods 40a, 40c are initially held in a first position by holding element 24 such that a sub-atmospheric pressure is maintained in headspace 16 within each syringe barrel 32a, 32b. Alternatively, piston rods 40a, 40c may be separated, so that sub-atmospheric pressure is maintained only in headspace 16 of syringe barrel 32a.

Further optionally, one or more of piston rods 40a, 40c may comprise more than one recess 70, located at different positions along piston rods 40a and/or 40c, to provide different optional pressure levels within headspace 16.

As further shown in FIG. 6B, controllers 20a, 20b are connected to a controller actuator 38, which when actuated (for example, pressed downwards by the user in a first step of operation of device 50), causes first controller 20a to change inlet 18a from a closed to an open state, allowing flow of solvent into syringe-barrel 32a of solid-containing unit 52, and causes second controller 20b to change inlet 18b from a closed to an open state, allowing flow of solvent into syringe barrel 32b. Optionally, a single controller 20 simultaneously changes inlets 18a and 18b from a closed position to an open position.

Holding element 24 optionally comprises or is connected to a holding element actuator 39, which when activated (for example, pressed downwards by the user in a second step of operation of device 50), causes at least one of movable seal elements 22a, 22c, to be released from holding element 24, enabling at least one movable seal element 22a, 22c, to move within the container. Optionally, each of moveable seal elements 22a, 22c, is released simultaneously from holding element 24. Alternatively, device 50 may comprise holding elements 24a, 24b, for individually holding each of moveable seal elements 22a, 22c, respectively. Holding element actuator 39 optionally activates single holding element 24 to release simultaneously each of moveable seal elements 22a, 22c. Alternatively, device 50 may comprise individual holding element actuators 39a, 39b, for actuation of holding elements 24a, 24b, respectively.

In some embodiments, in an initial position of device 50, each of syringe barrels 32a, 32b containing a solid composition has a sub-atmospheric pressure in the headspace 16, controller 20 (or controllers 20a, 20b) is closed, and piston rods 40a, 40c are held in a first position by holding element 24 to maintain sub-atmospheric pressure in headspace 16 of syringe barrels 32a, 32b, and to prevent suction of piston rods 40a, 40c into syringe barrels 32a, 32b due to the pressure difference between the atmospheric pressure of the environment and the sub-atmospheric pressure within headspace 16 of barrels 32a, 32b.

FIG. 7A illustrates a perspective and enlarged view of an embodiment of a holding element 24, comprising two bulges 72a, 72b, and a holding element actuator 39. Holding element 24 comprises a narrow base portion 74 and a wider upper portion 76. In such embodiments, holding element 24 is prevented from being pushed downwards in the channel-like structure formed by "U" shaped components 25 (shown in FIG. 6B), due to the width of upper portion 76.

FIG. 7B illustrates a perspective view of an embodiment of piston rods 40a, 40c of syringe barrels 32a, 32b of solid-containing unit 52 according to some embodiments disclosed herein. Recesses 70a, 70b are configured to engage bulges 72a, 72b, respectively.

Figure 8A:
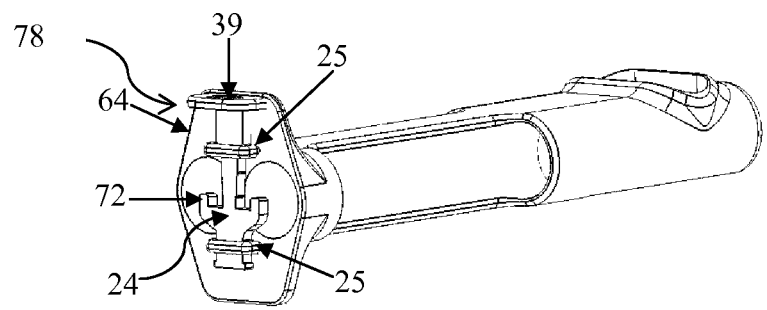
FIGS. 8A and B illustrate a side perspective view of the holding element of FIG. 6B located on a housing holding the solid-containing unit.
Figure 8B:
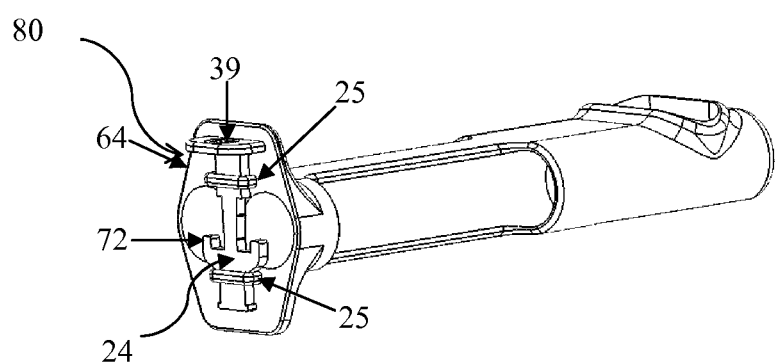

FIGS. 8A and 8B illustrate a perspective view of an embodiment of holding element 24 comprising bulges 72a, 72b, situated on a proximal end of housing 64 which holds together syringe barrels 32a, 32b of solid-containing unit 52. In FIG. 8A, holding element 24 is at a first position 78, prior to actuation, wherein bulges 72a, 72b are engaged within recesses 70a, 70b, respectively. In FIG. 8B, following actuation by holding element actuator 39, and disengagement of bulges 72a, 72b from recesses 70a, 70b, holding element 24 moves to a second position 80 on housing 64.

FIG. 9A illustrates an upper perspective view of an embodiment of holding element 24, at a first position 78, prior to activation, with two bulges 72a, 72b of holding element 24 engaged within two recesses 70a, 70b located at a fixed position along piston rods 40a, 40c, such that piston rods 40a, 40c are retained in a first position.

FIG. 9B illustrates a bottom perspective view of an embodiment of holding element 24 in the same position as in FIG. 9A.

FIG. 9C illustrates a bottom perspective view of an embodiment of holding element 24, at a second position 80, following actuation by holding element actuator 39, wherein bulges 72a, 72b are disengaged from recess 70a, 70b, thereby releasing holding element 24 from piston rods 40a, 40c, such that piston rods 40a, 40c are free to move within syringe barrels 32a, 32b, respectively.

FIG. 10 illustrates a side view of an embodiment of controller 20, having a substantially cylindrical portion 82 and a wider concave lower portion 84. Prior to actuation of controller 20, wider portion 84 is located in a flow path between syringe barrels 32a, 32b comprising the solid composition and syringe barrels 44a, 44b comprising the aqueous solvent, such that flow of solvent from syringe barrels 44a, 44b to syringe barrels 32a, 32b is physically blocked. When controller actuator 38 actuates controller 20, controller 20 is moved such that cylindrical portion 82 is located in the flow path and flow of solvent from syringe barrels 44a, 44b to syringe barrels 32a 32b can occur around cylindrical portion 82. In one embodiment, upon actuation of controller 20, the flow path remains open.

FIGS. 11A-C illustrate device 50 in an initial state, wherein solvent is contained within syringe barrels 44a, 44b, inlets 18a, 18b are in a closed position as maintained by controller 20. FIG. 11A shows an upper view; FIG. 11B shows a cross-sectional side view; and FIG. 11C shows an enlarged view of the area comprising controller 20. In this figure piston rods 40a, 40c are in an initial position to maintain the volume of headspace 16 such that the pressure in headspace 16 is maintained at a sub-atmospheric pressure. Subsequently, controller actuator 38 is activated so that controller 20 changes inlets 18a, 18b from a closed position to an open position, such as by removal of a wider concave lower portion 84 of controller 20 from the flow path. Piston rods 40b, 40d of solvent-containing unit 54 are drawn into syringe barrels 44a, 44b due to the difference in pressure between the atmospheric pressure of the surrounding environment and the sub-atmospheric pressure in headspace 16 within syringes 32a, 32b, such that solvent flows from syringe barrels 44a, 44b to syringe barrels 32a, 32b, respectively.

FIGS. 12A-C illustrate device 50 after transfer of solvent from syringe barrels 44a, 44b to syringe barrels 32a, 32b. FIG. 12A shows an upper view; FIG. 12B shows a cross-sectional sided view; and FIG. 12C shows an enlarged view of the area comprising controller 20. During this step, the substantially cylindrical portion 82 of controller 20 is located in the fluid flow path.

FIG. 13 illustrates solvent-containing unit 54, disconnected from solid-containing unit 52 and connected to a fluid connector system 86 including fluid connectors 60, 62 comprising luer fittings through which the solutions formed from dissolution of the two solid compositions in the solvent can be administered to a subject. Fluid connector system 86 may optionally comprise a catheter having multiple lumens to provide multiple flow channels.

FIG. 14A illustrates an embodiment of holding element 24 comprising a spacer 88 having a tunnel-like structure 90, optionally comprising a rigid material, and configured to be positioned on piston rods 40a, 40c of the solid-containing unit 52, optionally between a back end of piston rods 40a, 40c and of syringe barrel 32 containing the solid compositions.

FIG. 14B illustrates spacer 88 positioned on piston rod 40 of a syringe barrel 32 of solid-containing unit 52. In such an embodiment, spacer 88 prevents piston rod 40 from being drawn into syringe barrel 32. Upon removal of spacer 88 from piston rod 40, piston rod 40 is released and drawn into syringe barrel 32. The length and position of spacer 88 is determined according to the volume of headspace 16 which is required within syringe barrel 32 in order to provide a required pressure within headspace 16.

In some embodiments, the operating sequence of device 50 includes the following steps:

In an initial position, solid-containing unit 52 and liquid/solvent-containing unit 54 are connected to one another (e.g. via fluid connectors 60, 62 comprising luer fittings) configured to provide fluid communication between syringe barrels 44a, 44b of solvent-containing unit 54, and syringe barrels 32a, 32b of solid-containing unit 52. At this stage, inlets 18a, 18b are closed, preventing fluid flow from syringe barrels 44a, 44b to syringe barrels 32a, 32b. The volume occupied by the solvent in syringe barrels 44a, 44b, is smaller than the volume occupied by the solid compositions in syringe barrels 32a, 32b. The pressure in the headspace 16 within syringe barrels 32a, 32b is sub-atmospheric. The pressure within a headspace in syringe barrels 44a, 44b is equal to the environmental pressure e.g. atmospheric pressure. The piston rods 40a, 40c of the syringes of solid-containing unit 52 are retained in their initial position partially enclosed within their corresponding barrels using a holding element 24 as elaborated above.

In a first step, the user activates controller actuator 38, for example by pressing downwards, thereby actuating controllers 20a, 20b and opening inlets 18a, 18b and outlets 46a, 46b, thereby allowing flow of solvent from syringe barrel 44a to syringe barrel 32a, and from syringe barrel 44b to syringe barrel 32b. When the solvent flows into syringe barrels 32a, 32b the pressure within headspace 16 in barrels 32a, 32b remains at a sub-atmospheric level.

In one embodiment, after activating controller actuator 38, the fluid connection remains open.

At a second stage, after all the solvent is introduced into syringe barrels 32a, 32b, the user activates holding element actuator 39 (which is optionally a part of holding element 24), resulting in release of piston rods 40a, 40c of solid-containing unit 52. Subsequently, piston rods 40a, 40c are drawn into their corresponding syringe barrels 32a, 32b by virtue of the lower pressure in syringe barrels 32a, 32b with respect to the atmospheric pressure of the environment, thereby resulting in an increase of pressure within headspace 16 of barrels 32a, 32b until the pressure within headspace 16 is equal to atmospheric pressure.

According to the principles disclosed herein, the increase in pressure is achieved by decreasing the headspace in syringe barrels 32a, 32b without introducing gas into the syringes. Advantageously, the change in the pressure level within headspace 16 substantially eliminates or minimizes foam formation and enables agitation of the suspension of the solid composition in the solvent in an almost complete absence of foam.

The suspension can be agitated using piston rods 40a, 40b, 40c, 40d, by transferring the suspension between syringe barrels 44a and 32a, and between syringe barrels 44b and 32b several times to facilitate the complete dissolution and form a solution wherein the solid composition is fully dissolved in the solvent. After dissolution or reconstitution is completed, the user can disconnect unit 52 from unit 54 and administer the reconstituted solution to a desired location e.g. by connecting a fluid connector system 86, through which the two reconstituted solution can be delivered.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

EXAMPLES

Materials and Methods:
Lyophilization.

The lyophilization was carried out according to the cycle shown in Table 1 using a Christ Epsilon 2-8D lyophilizer. The lyophilization was carried out in cylindrical vials or cups, which were sealed upon completion of the lyophilization process. The lyophilization process produced a solid, three-dimensional fibrinogen "cake".

TABLE 1

| Section | Phase | Time (h:m) | Temp (° C.) | Vacuum (mBar) |
|---|---|---|---|---|
| 1 | Start values | —:— | 4 | OFF |
| 2 | Freezing | 1:00 | −30 | OFF |
| 3 | Freezing | 1:00 | −50 | OFF |
| 4 | Freezing | 5:40 | −50 | OFF |
| 5 | Preparation | 0:20 | −45 | OFF |
| 6 | Sublimation | 0:15 | −42 | 0.2 |
| 7 | Sublimation | 0:15 | −25 | 0.2 |
| 8 | Sublimation | 25:00 | −25 | 0.2 |
| 9 | Sublimation | 1:00 | −15 | 0.2 |
| 10 | Sublimation | 12:00 | −15 | 0.2 |
| 11 | Second drying | 2:00 | 20 | 0.2 |
| 12 | Second drying | 5:00 | 20 | 0.2 |
| 13 | Second drying | 18:30 | 25 | 0.12 |

Optionally, a pressure of higher than 0.12 mBar may be provided by increasing the pressure in the lyophilization vial to the desired pressure subsequent to step 13, prior to sealing the lyophilization vial.

Clauss Clotting Time Method.

This method measures clottable fibrinogen concentration in a sample according to its clotting time in the presence of a constant amount of thrombin using a clotting time machine (Diagnostica Stago Inc., USA). The clotting time measured for the sample is compared to that obtained with a calibration curve produced with a fibrinogen standard. The method used is a modification of the Eu. Ph. assay 0903/1997 as elaborated in: European Pharmacopaiea, Fibrin sealant kit. 1997; 0903: 858; and Clauss A. Gerinnungsphysiologische Schnellmethode zur Bestimmung des Fibrinogens. Acta Haematol. 1957; 17: 237-246.

Preparation of Degassed Double Distilled Water (Degassed DDW).

Double Distilled Water (DDW) was stirred under vacuum until no more air bubbles emerged above the surface of the water.

Fibrinogen Stock Solution.

Biological active component (BAC) solution as in EVICEL® Fibrin Sealant (Omrix Biopharmaceuticals Ltd.) having a clottable fibrinogen concentration of 55-85 mg/ml was used as the fibrinogen stock solution in all the experiments described below.

Measurements of Protein Dissolution Level.

Optical density (OD) was measured for fibrinogen test solutions following lyophilization and dissolution, and for control solution comprising BAC fibrinogen stock solution which was not subjected to lyophilization and dissolution.

A sample of 150 μl from each fibrinogen test solution was diluted 1:400 with DDW, and OD was measured at 280-320 nm against a DDW blank. The measurement was carried out in acrylic cuvettes (Sarstedt, Germany; Cat. number 67.740) using ULTRASPEC 2100pro spectrophotometer (Amersham Pharmacia Biotech, Sweden).

OD of the control solution was considered to be 100%. The calculations were made according to the following formula, with the results expressed in percent:

$$\text{Protein dissolution level} = \frac{\text{Test solution } OD280\text{-}OD320}{\text{Control solution } OD280\text{-}OD320} \times 100$$

Example 1

Dissolving Solid Fibrinogen to Obtain Concentrated Fibrinogen Solutions

The effect of fibrinogen density of a solid three-dimensional fibrinogen low-density "cake" obtained by lyophilization as described above on the level of protein dissolution in aqueous solvent was examined. The protein density in a "cake" obtained from a protein solution after lyophilization, as expressed in mg/cc, is substantially equivalent to the protein concentration in the solution in mg/ml prior to lyophilization. Hence, dilution of a stock solution prior to lyophilization results in a "cake" of lower density than that of a "cake" obtained by lyophilzation of the undiluted stock solution. The volume of the "cake" is substantially equal to the volume of the solution from which the "cake" was prepared. Therefore, dissolution of the "cake" in a volume that is equal to the volume of the "cake" results in a solution having a concentration equivalent to that of the solution from which the "cake" was prepared, while dissolution of the "cake" in a volume which is lower than the volume of the solid "cake" results in a solution having a concentration greater than that of the solution from which the "cake" was prepared.

For preparing low-density "cakes" with different fibrinogen densities, fibrinogen stock solution comprising 63 mg/ml fibrinogen (as described in the Materials and Methods section above) was diluted with DDW to obtain fibrinogen solutions having concentrations in the range of 21-42 mg/ml. Diluted solutions and a control sample comprising non-diluted fibrinogen stock solution were lyophilized, yielding "cakes" having different fibrinogen densities. The "cakes" were dissolved in aqueous solvent and the level of protein dissolution was measured as described below.

More specifically, 5 ml of stock solution was diluted with DDW to yield diluted solutions having clottable fibrinogen concentrations of 42, 32, and 21 mg/ml and final volumes of 7.5, and 15 ml, respectively. In the next step, 5 ml of a control sample comprising fibrinogen stock solution and the final volumes of diluted solutions were each transferred into cylindrical glass cups (diameter: 30 mm/height: 25 mm), designed to produce cakes able to fit within a syringe, and subjected to lyophilization according to the cycle described in the Materials and Methods section. In this experiment, the cylindrical glass cups were not capped.

At the end of the lyophilization cycle, dry lyophilized "cakes" having fibrinogen densities of 63 (from control sample), 42, 32, and 21 mg/cc (from diluted test samples) were obtained. Each "cake" was removed from the cylindrical glass cup and fitted into the barrel of a 50 ml syringe (PIC Indolor, Italy) by removing the plunger of the syringe, inserting the "cake" into the barrel of the syringe, and then replacing the plunger in the barrel. The 50 ml syringe was connected to a first connection point of a three way stop cock (Medipharm, UK), a 5 ml syringe (TERUMO, Belgium) containing 5 ml degassed DDW (prepared as described above) was connected to the second connection point of the stop cock, and a 20 µm filter (MDI, India; Cat. number SYPP0611MNXX104) was connected to the third connection point.

Each of the low-density "cakes" obtained from the diluted solutions was dissolved in 5 ml DDW at a temperature of 22±2° C. in order to obtain solutions having a final fibrinogen concentration of 63 mg/ml (similar to the concentration of the fibrinogen stock solution which is used inter alia as a hemostat) in one of the following methods:

Method 1: The three way stop cock was set to allow fluid communication between the 5 ml syringe containing the degassed DDW and the 50 ml syringe containing the low-density "cake" and the degassed DDW was introduced into the 50 ml syringe. Following introduction of the degassed DDW into the 50 ml syringe, the solution comprising partially dissolved fibrinogen thus formed was transferred from one syringe to the other three times by moving the plungers of the syringes back and forth, in order to enhance dissolution of the fibrinogen. The syringe assembly was incubated at room temperature for two minutes to obtain a solution comprising substantially completely dissolved fibrinogen. The overall time from the introduction of the degassed DDW up to the end of the incubation was about 150 seconds. Subsequently, the three way stop cock was set to allow flow of the fibrinogen solution through the 20 µm filter in order to remove un-dissolved particles from the solution.

Method 2: The dissolution was carried out in a similar manner to that described above in Method 1, but with the solution comprising partially dissolved fibrinogen being transferred from one syringe to the other five times and the resulting solution was immediately filtered without any incubation period. The time from the introduction of the degassed DDW until the end of the fifth transfer of the solution between the two syringes was about 30 seconds.

The percentage of dissolved protein in the solution was measured as described above in the Materials and Methods section under "Measurements of Protein dissolution level". The results are shown in Table 2 below.

TABLE 2

| Fibrinogen density within the lyophilized "cake" (mg/cc) | Protein dissolution ± SD (%) | |
|---|---|---|
| | By method 1 Mixed 3 times and incubated | By method 2 Mixed 5 times with no incubation |
| 63 | 12.3 ± 4.6 | 15.3 ± 7 |
| 42 | 28.1 ± 7.4 | 25 ± 9.9 |
| 32 | 51.6 ± 7.5 | 29.8 ± 5.2 |
| 21 | 81.8 ± 8.2 | 43 ± 2.3 |

* The measurements were carried out in triplicate

It was observed that dissolving a lower protein density "cake" in water resulted in increased percentage of protein dissolution as compared to that obtained with a higher protein density "cake" in both dissolution methods. In this experiment, optimal protein dissolution was obtained while dissolving a lyophilized "cake" having a fibrinogen density of 21 mg/cc by using method 1 which includes incubation and lasts 150 seconds. The results show that incubation and mixing or agitation is important and that a relatively long period of time is required to dissolve the solid fibrinogen preparation. Of note, the fibrinogen density within the lyophilized "cake" can be decreased to 5 mg/cc while maintaining the stability of the lyophilizate without any collapse of the "cake" (Parker et. al. "Determination of the influence of primary drying rates on the microscale structural attributes and physicochemical properties of protein containing lyophilized products". J Pharm Sci. 2010; 99:4616-4629).

A visual inspection of the solution revealed that dissolution of the lyophilized "cakes" in the manner described above resulted in formation of a foamy solution.

Example 2

The Effect of Pressure on Foam Disappearance Rate During Dissolution

The effect of pressure on the rate of disappearance of foam formed during dissolution of lyophilized low-density fibrinogen "cake" was studied, using sub-atmospheric pressure conditions, followed by equilibration to atmospheric pressure (1000 mBar).

For this purpose, "cakes" having a fibrinogen density of 21 mg/cc were prepared. Eight test solutions, each of volume 15 ml and having a clottable fibrinogen concentration of 21 mg/ml, were prepared by diluting 5 ml stock solution having fibrinogen concentration of 63 mg/ml, as described above, with 10 ml DDW. The solutions were each lyophilized in a 50 ml glass vial. The eight lyophilization vials were partially covered with rubber caps, and lyophilized as described in Table 1 in the Materials and Methods section. At the end of the lyophilization cycle, dry "cakes" having a fibrinogen density of 21 mg/cc were obtained.

The "cakes" were subjected to the following sub-atmospheric pressures: 0.12, 100, 250, or 500 mBar. For this purpose, the glass vials containing the "cakes" were sealed and capped by adjusting the pressure within the lyophilizer to the required pressure and lowering the lyophilizer shelf on the rubber caps. Samples for testing at each pressure were provided in duplicate.

The "cakes" of the test samples were then dissolved in DDW at room temperature (22±2° C.) to provide solutions having a fibrinogen concentration of 63 mg/ml as follows. First, 4.4 ml degassed DDW were injected through the rubber cap into the vial containing the "cake", using a 5 ml syringe (Terumo, Belgium) connected to a 23G needle (Medi plus, China), while maintaining the pressure in the vial at the specified sub-atmospheric pressure. The needle was allowed to remain within the rubber cap following the injection. Twenty seconds after injection of the degassed DDW into the vial, the pressure in the vial was equalized to atmospheric pressure by disconnecting the syringe from the needle and letting air from the surrounding area enter the vial via the needle. One sample at each pressure level was dissolved in this manner.

Dissolution of the "cakes" of the second (control) sample at each pressure level was carried out by injecting degassed DDW at a temperature of 22±2° C., at atmospheric pressure, as follows: First, the cap of the vial was opened slightly in order to bring the pressure within the vial to atmospheric pressure, and then 4.4 ml degassed DDW were added to the vial to achieve a concentration of 63 mg/ml clottable fibrinogen (as for that of stock solution). The time required for the foam to disappear was measured from the time of addition of the degassed DDW to the lyophilized low-density "cake"

up to the time at which a third of the surface area of the dissolved solution was visible from above. The results are shown in Table 3 below.

TABLE 3

| Dissolution method | Pressure level within the vial at the time of DDW injection and after up to 20 seconds (mBar) | Pressure level within the vial 20 seconds after DDW injection*** (mBar) | Foam disappearance time ± SD (sec)** |
|---|---|---|---|
| Dissolution under low pressure followed by equilibration to atmospheric pressure* | 0.12 | 1000 | 30.50 ± 6.95 |
| | 100 | 1000 | 160.70 ± 203.0 |
| | 250 | 1000 | 622.25 ± 158.51 |
| | 500 | 1000 | 801.25 ± 428.54 |
| Control* | 1000 | 1000 | 5,235 ± 2533.48 |

*The measurements were carried out in triplicate.
**From the introduction of the degassed DDW up to the point in which a third of the surface area of the dissolved solution was visible from above.
***Increase in pressure level to 1000 mBar is accompanied by increase in air within the vial.

It was observed that dissolution of lyophilized fibrinogen "cake" at sub-atmospheric pressure followed by equilibration to atmospheric pressure enhanced foam disappearance rate as compared to the control group (injection of degassed DDW under atmospheric pressure). The pressure level within the vial during the addition of the degassed DDW was shown to be directly correlated to the foam disappearance time (i.e. low pressure within the vial during addition of the degassed DDW resulted in a short foam disappearance time). In this experiment, optimal results were observed by adding DDW to the low density "cake" at a pressure of 0.12 mBar, incubating for 20 seconds, followed by equilibrating to atmospheric pressure.

These results show that in order to minimize the presence of foam during dissolution of lyophilized fibrinogen "cake", the solvent is advantageously added under sub-atmospheric pressure followed by equilibration to atmospheric pressure.

Example 3

The Effect of Agitating the Solution on Foam Formation, Protein Dissolution Level and Dissolution Rate The previous experiment shows that dissolving lyophilized low density "cake" at sub-atmospheric pressure followed by introducing air into the vial and equilibrating the pressure in the lyophilization vial to atmospheric pressure results in shorter foam disappearance time.

Agitating a mixture is desirable for shortening the dissolution time and for obtaining a homogeneous solution. In the following experiments, equilibration to atmospheric pressure was carried out mechanically without introducing air into the vial and then the effect of agitating the solution on protein dissolution level, dissolution rate, and foam disappearance was examined Agitation of the solution was carried out by two different methods: A—by using two connected syringes and transferring the solution from one syringe to the other (i.e. by using a reciprocating mixing device); or B—by manually shaking the vessel containing the solution. In both experiments, the dissolution was carried out at room temperature (22±2° C.) and the added DDW was at a temperature of 22±2° C.

A. Agitating the Solution by a Reciprocating Mixing Device—

Low density "cakes" were prepared as follows. 4 ml fibrinogen stock solution having 63 mg/ml clottable fibrinogen was diluted with DDW to obtain solutions having a clottable fibrinogen concentration of 48, 32 and 21 mg/ml. Final volumes of 6, 8, and 12 ml, respectively, were obtained following the dilution step. In the next step, 4 ml of each of a non-diluted fibrinogen stock solution, and the final volume of the diluted solutions were lyophilized according to the cycle described in the Materials and Methods section. The lyophilization procedure was carried out in specially designed cylindrical glass cups (diameter: 23 mm/height: 25 mm).

In cases where the final volume of the diluted solution was higher than the volume of the glass cup (5 ml), the diluted solution was lyophilized in more than one glass cup (i.e. 63 mg/ml-1 cup, 48 mg/ml-2 cups, 32 mg/ml-2 cups, 21 mg/ml-3 cups). In this experiment, the cylindrical glass cups were not capped or sealed under sub-atmospheric pressure conditions at the end of the lyophilization cycle. The lyophilization of the four different fibrinogen solutions yielded lyophilized "cakes" having fibrinogen densities of 63 48, 32, and 21 mg/cc. Then, each obtained lyophilized "cake" was fitted into a 12 ml syringe by removing the plunger of the syringe, inserting the "cake" into the barrel of the syringe, and returning the plunger to the barrel. In cases where more than more than one cup was used for the lyophilization, all the obtained cakes were inserted into the same barrel. The 12 ml syringe was connected to a first connection point of a three way stop cock (Medipharm, UK), a second 12 ml containing approximately 3.6 ml degassed DDW (prepared as described in the Materials and Methods section) was connected to the second connection point of the stop cock, and a vacuum pump (KNF Neuberger, Germany) was connected with a vacuum manometer (Fisher Scientific, USA) to the third connection point.

The low density "cakes" were then subjected to sub-atmospheric pressure levels. For this purpose, the three way stop cock was set to allow fluid communication between the vacuum pump and the 12 ml syringe holding the lyophilized "cake"; and the plunger of the 12 ml syringe which held the lyophilized "cake" was retained at the top of the syringe barrel by an aluminum spacer to hold the plunger in place and prevent it from being drawn into the barrel of the syringe during the step of subjecting the low density "cakes" to sub-atmospheric pressure. Air was then drawn out of the 12 ml syringe holding the lyophilized "cake" by the vacuum pump to provide a predetermined pressure of 25, 200 or 500 mBar. In another tested group, air was not drawn out of the barrel of the syringe, such that the pressure within the syringe was 1000 mBar.

The lyophilized "cakes" were dissolved in DDW to provide a solution having a fibrinogen concentration of 63 mg/ml (as in the non diluted stock solution) using the following method: First, the three way stop cock was set to allow fluid communication between the 12 ml syringe holding the degassed DDW (3.6 ml) and the 12 ml syringe holding the lyophilized "cake", resulting in flow of the degassed DDW into the syringe holding the lyophilized "cake" and providing a solution comprising partially dissolved fibrinogen, while maintaining a sub-atmospheric pressure. In this step, the pressure within the syringe holding the solution comprising partially dissolved fibrinogen increased with regard to the pressure during the earlier step, but was still lower than the atmospheric pressure. Then, the pressure within the syringe was equilibrated to atmospheric pressure in the absence of air by removing the aluminum spacer from the plunger, and letting the plunger be drawn into the barrel or by pushing the plunger. The equilibration of the pressure was hence carried out mechanically without introducing air or gas, as opposed to Example 2 wherein equilibration with the atmospheric pressure was carried out by introducing air from the surrounding area into the vial. The syringe assembly was then left to stand with the solution comprising partially dissolved fibrinogen for 30 seconds and at the same time the vacuum pump was disconnected from the three way stop cock. In the next step, the solution comprising partially dissolved fibrinogen was agitated by transferring the solution from one syringe to the other 10 times at a rate of 3.8 cm/sec by using a customised dissolution machine, to obtain a solution comprising substantially completely dissolved fibrinogen. Briefly, the customized dissolution machine comprises two syringe pumps facing each other, each containing a syringe. The syringes of the two syringe pumps are connected together with a connecting element containing a valve to control the passage of water and maintain the vacuum within the solid-containing syringe. The two syringe pumps work in synchronization such that when the first syringe pump pulls the plunger of the first syringe, the second syringe pump pushes the plunger of the second syringe and vice versa.

Afterwards, the syringe holding the solution comprising substantially completely dissolved fibrinogen was disconnected from the three way stop cock, and the solution was filtered through a 20 μm filter to separate any un-dissolved material from the solution.

Dissolution of lyophilized low-density "cakes" under atmospheric pressure was carried out in the same manner described above except that an aluminum spacer was not used and the pressure during the entire dissolution step was equal to the atmospheric pressure. The time from the introduction of the degassed DDW until the end of the tenth time the solution was transferred between the two syringes was 45 seconds.

To evaluate the ability of the solid proteins to dissolve under the above described conditions, the protein dissolution level within the dissolved solution was measured as described above in the Materials and Methods section under "Measurements of Protein dissolution level". The presence of foam was visually inspected.

The results are shown in Table 4 below.

TABLE 4

| Fibrinogen density within the lyophilized | Pressure level within the vial at the time of DDW addition (mBar) | | | |
|---|---|---|---|---|
| "cake" (mg/cc) | 1000 | 500 | 200 | 25 |
| 63 | 63 | 72 | 51 | 69 |
|  | 62 | 83 | 46 | 87 |
|  | 59 | stuck | 60 | 82 |
|  | stuck | stuck | stuck | 78 |
|  | stuck | stuck | stuck | 84 |
|  | 61 ± 2 | 78 ± 8 | 52 ± 7 | 80 ± 7 |
| 42 | 70 | 77 | 91 | 97 |
|  | 71 | 80 | 77 | 83 |
|  | 80 | 82 | 80 | 74 |
|  | stuck | stuck | stuck | 96 |
|  | stuck | stuck | stuck | 90 |
|  | 74 ± 5 | 79 ± 2 | 82 ± 7 | 88 ± 10 |
| 32 | 86 | 78 | 87 | 89 |
|  | 77 | 81 | 92 | 103 |
|  | 88 | 91 | 87 | 102 |
|  | 81 | 91 | 87 | 107 |

TABLE 4-continued

| Fibrinogen density within the lyophilized | Pressure level within the vial at the time of DDW addition (mBar) | | | |
|---|---|---|---|---|
| "cake" (mg/cc) | 1000 | 500 | 200 | 25 |
|  | stuck | 88 | 87 | 94 |
|  | 83 ± 5 | 86 ± 5 | 88 ± 2 | 99 ± 7 |
| 21 | 94 | 96 | 88 | 92 |
|  | 90 | 92 | 96 | 100 |
|  | 87 | 93 | 87 | 102 |
|  | 96 | 95 | 93 | 100 |
|  | 90 | 91 | 89 | 104 |
|  | 91 ± 3 | 94 ± 2 | 90 ± 4 | 100 ± 5 |

\* Stuck means that the dissolution machine was unable to move the plungers due to blockage of the syringes by un-dissolved particles.
\*\* Each experiment was carried out in 5 replicates.

The results show that dissolution of lyophilized "cake" having a fibrinogen density of lower than 42 mg/cc e.g. 32 mg/cc or 21 mg/cc under a pressure of lower than 200 mBar e.g. 25 mBar followed by equilibration to atmospheric pressure without introducing air, and agitating the solution (e.g. by reciprocating the solution between two syringes) resulted in 100% protein dissolution within a short time of 45 seconds. No significant amount of foam was observed following dissolution under a pressure of 25 mBar while higher pressure levels resulted in significant foam formation.

B—Agitating by Manually Shaking the Vessel Containing the Solution.

The agitating was carried out by manually shaking the syringe containing the solution in the presence of stainless steel spheres.

For examining the effect of manual shaking, lyophilized "cakes" having fibrinogen densities 23, 35, 47, and 70 mg/cc were prepared from fibrinogen solutions having a fibrinogen concentration of 23, 35, 47, and 70 mg/ml, respectively, in the manner described above. Briefly, 4 ml fibrinogen stock solution was diluted to a fibrinogen concentration of 23, 35, 47 mg/ml with DDW, as described above. The total volume of each diluted fibrinogen solution and a 4 ml sample of non-diluted fibrinogen stock solution were lyophilized according to the lyophilization cycle described in Table 1. The vials containing the lyophilized "cakes" were not capped or sealed under low pressure conditions at the end of the lyophilization cycle. The obtained low-density "cakes" were inserted into the barrel of a 12 ml syringe as described above together with 4 stainless steel spheres. Two different stainless steel spheres were used in this experiment: a 4 mm diameter sphere (weighing 260 mg) and a 6.4 mm diameter.

The 12 ml syringe was connected to a first connection point of a three way stop cock (Medipharm, UK), a 5 ml syringe (TERUMO, Belgium) containing 4.35 ml degassed DDW (prepared as described above) was connected to the second connection point of the stop cock, and a vacuum pump (KNF Neuberger, Germany) was connected with a vacuum manometer (Fisher Scientific, USA) to the third connection point.

Then, the low density "cakes" were subjected to a pressure level of 25 mBar. For this, the three way stop cock was set to allow fluid communication between the syringe holding the lyophilized "cake" and the vacuum pump, and the plunger of the syringe holding the "cake" was fixed in place at the top of the barrel of the syringe by a spacer as described above. Air was then drawn out of the syringe holding the lyophilized "cake" by the vacuum pump until a pressure of 25 mBar was reached. Following drawing of the air, the three way stop cock was set to allow fluid communication from the syringe holding the degassed DDW to the syringe holding the lyophilized "cake" to obtain a solution comprising partially-dissolved fibrinogen. The aluminum spacer was removed, resulting in equilibration of the pressure within the syringe holding the solution with atmospheric pressure without introducing air into the syringe. Thirty seconds after introduction of the degassed DDW to the "cake", the syringe containing the solution comprising partially-dissolved fibrinogen was disconnected from the syringe assembly together with the three way stop cock and shaken manually for 60 seconds leading to movement of stainless steel spheres within the barrel, and providing a solution comprising substantially completely dissolved fibrinogen. The time from the introduction of the degassed DDW until the end of the manual shaking step was about 90 seconds.

Then, the three way stop cock was connected to a 20 μm filter, and the solution comprising substantially completely dissolved fibrinogen was filtered to separate any un-dissolved material from the solution. The percentage of protein dissolution was determined as described above. The presence of foam was visually inspected.

The experiment was carried out in triplicate for each tested group. The results are shown in Table 5.

TABLE 5

| Fibrinogen density within the lyophilized "cake"(mg/cc) | Protein dissolution ± SD (%) | |
|---|---|---|
| | Sphere Diameter (mm) | |
| | 4 | 6.4 |
| 70 | 58 ± 8 | 65 ± 18 |
| 47 | 90 ± 4 | 100 ± 3 |
| 35 | 83 ± 3 | 103 ± 3 |
| 23 | 92 ± 5 | 97 ± 3 |

It can be seen that complete protein dissolution was obtained within a short time of 90 seconds by dissolving a lyophilized "cake" having a low fibrinogen density (e.g. equal to or lower than 47 mg/cc) at a low pressure of 25 mBar, followed by equilibration to atmospheric pressure without introducing air, and by hand shaking the solution with large spheres e.g. having a diameter of 6.4 mm. No significant amount of foam was observed in any of the tested groups.

By comparison, in Example 1 which examines the effect of protein density within the lyophilized "cake" on protein dissolution level, complete protein dissolution (97.4±9.8%) was obtained within 150 seconds which is about 1.7-3.4 times longer than the time required for complete dissolution in these experiments (45 or 90 seconds).

What is claimed is:

1. A method for dissolving a solid fibrinogen composition in an aqueous solvent while minimizing or avoiding the presence of foam, comprising:

i) providing a closed container containing: a volume of the solid fibrinogen composition and a head space, wherein the internal pressure within the headspace is a sub-atmospheric pressure being not more than 500 mBar;

ii) while maintaining the internal pressure in the headspace at the sub-atmospheric pressure, introducing into the container a volume of the aqueous solvent which is less than the volume of the solid fibrinogen composition to form a solution comprising at least 40 mg fibrinogen/ml, wherein the pressure in the headspace is maintained at the sub-atmospheric level after introducing the entire volume of the aqueous solvent into the container;

iii) subsequent to ii), decreasing the size of the headspace in the container by decreasing the internal volume of the container and without allowing entry of air into the container until the internal pressure in the headspace equals atmospheric pressure; and iv) agitating the solution until the fibrinogen dissolves, wherein the aqueous solvent is contained within a reservoir,
   wherein the container and the reservoir are in mutual fluid communication,
   wherein the agitating comprises repeatedly transferring the aqueous solvent between the container and the reservoir and
   wherein the dissolving is carried out over a period of up to 90 sec.

2. The method according to claim 1, wherein the solid fibrinogen composition is a lyophilized cake.

3. The method according to claim 1, wherein the density of fibrinogen in the solid fibrinogen composition is in the range of from at least 5 to lower than 63 mg/cc.

4. The method according to claim 3, wherein the density of fibrinogen is not more than 23 mg/cc.

5. The method according to claim 1, wherein the fibrinogen concentration in the obtained solution is from 40 mg/ml to 120 mg/ml.

6. The method according to claim 1, wherein the aqueous solvent is a degassed aqueous solvent.

7. The method according to claim 1, wherein the internal pressure in the headspace in step i) is not more than 0.12 mBar.

8. The method according to claim 1, when a time interval of at least 5 seconds is allowed to elapse between completion of step ii) and commencement of step iii).

9. The method according to claim 8, wherein the time interval is at least 20 seconds.

10. The method according to claim 1, further comprising incubating the solution in the container.

11. The method according to claim 10, wherein the incubating is carried out for no longer than 2 minutes.

* * * * *